United States Patent [19]
Kelley et al.

[11] Patent Number: 5,919,643
[45] Date of Patent: Jul. 6, 1999

[54] METHODS AND COMPOSITIONS FOR THE USE OF APURINIC/APYRIMIDINIC ENDONUCLEASES

[75] Inventors: Mark R. Kelley, Zionsville; John Duguid, Brownsburg; John Eble, Indianapolis, all of Ind.

[73] Assignee: Advanced Research & Technology Institute, Bloomington, Ind.

[21] Appl. No.: 08/872,719

[22] Filed: Jun. 11, 1997

Related U.S. Application Data

[60] Provisional application No. 60/019,561, Jun. 11, 1996, and provisional application No. 60/019,602, Jun. 11, 1996.

[51] Int. Cl.$^6$ .................................. C12Q 1/44; C12N 9/22
[52] U.S. Cl. ............................................. 435/19; 435/199
[58] Field of Search ....................................... 435/19, 199

[56] References Cited

U.S. PATENT DOCUMENTS

| | | | |
|---|---|---|---|
| 4,618,585 | 10/1986 | Chan | 435/240 |
| 4,633,886 | 1/1987 | Bucaro, Jr. | 128/749 |
| 4,666,845 | 5/1987 | Mattes et al. | 435/240 |
| 4,862,899 | 9/1989 | Bucaro | 128/749 |
| 5,171,666 | 12/1992 | Gutowski et al. | 530/387.3 |
| 5,306,811 | 4/1994 | Duffy | 530/412 |
| 5,320,956 | 6/1994 | Willingham et al. | 435/172.2 |
| 5,330,972 | 7/1994 | Cope | 514/2 |
| 5,360,893 | 11/1994 | Owens et al. | 530/350 |
| 5,399,586 | 3/1995 | Davies et al. | 514/448 |
| 5,403,717 | 4/1995 | Holmes | 435/7.25 |

OTHER PUBLICATIONS

Ali et al., "Heterogeneity of subcellular localization of p53 protein in human glioblastomas," *Cancer Res.*, 54:1–5, 1994.

Bamford, et al. "An immunohistochemical study of the distribution of epithelial antigens in the uterine cervix," *Obstetrics & Gynecology*, 61(5):603–608, 1983.

Battaglia et al., "Immunosuppressive acidic protein (IAP) and squamous cell carcinoma antigen (SCC) in patients with cervical cancer," *Gynecol. Oncol.*, 53:176–182, 1994.

Bosari et al., "Cytoplasmic accumulation of p53 protein: an independent prognostic indicator in colorectal adenocarcinomas," *J. Nat'l. Cancer Instit.*, 86(9):681–687, 1994.

Bychkov et al., "Immunocytochemical localization of carcinoembryonic antigen (CEA), alphafetoprotein (AFP) and Human chorionic gonadotropin (HCG) in cervical neoplasia," *Am. J. Clin. Pathol.*, 79(4):414–420, 1983.

Demple et al., "Cloning and expression of APE, the cDNA encoding the major human apurinic endonuclease: Definition of a family of DNA repair enzymes," *Biochem.*, 88:11450–11454, 1991.

Duguid et al., "Differential cellular and subcellular expression of the human multifunctional apurinic/apyrimidinic endonuclease (APE/ref-1) DNA repair enzyme," *Cancer Res.*, 55:6097–6102, 1995.

Duk et al., "Cancer of the uterine cervix: Sensitivity and specificity of serum squamous cell carcinoma antigen determinations," *Gynecol. Oncol.*, 39:186–194, 1990.

Emanuele et al., "In vivo effect of ethanol on release of LH–releasing hormone and LH in rats," *J. Endocrinol.*, 121:37–41, 1989.

Emanuele et al., "In vivo effects of acute EtOH on rat α and β luteinizing hormone gene expression," *Alcohol*, 8:345–348, 1991.

Emanuele et al., "The effect of acute in vivo ethanol exposure on follicle stimulating hormone transcription and translation," *Alcohol Clin. Exp. Res.*, 16(4):776–780, 1992.

Emanuele et al., "The effect of 'binge' ethanol exposure on growth hormone and prolactin gene expression and secretion," *Endocrinol.*, 131(5):2077–2082, 1992.

Gocze et al., "Serum levels of squamous cell carcinoma antigen and ovarian carcinoma antigen (CA 125) in patients with benign and malignant diseases of the uterine cervix," *Oncol.*, 51:430–434, 1994.

Hale et al., "Prognostic value of epidermal growth factor receptor expression in cervical carcinoma," *J. Clin. Pathol.*, 46:149–153, 1993.

Henner et al., "Purification and amino–terminal amino acid sequence of an apurinic/apyrimidinic endonuclease from calf thymus," *Nucl. Acids Res.*, 15(14):5529–5544, 1987.

Hughes–Davies et al., "Expression of the human apurinic endonuclease gene (APE) in normal and malignant tissues," *Int'l. J. Oncol.*, 6:749–752, 1995.

International Search Report dated Nov. 11, 1997 (PCT/US97/10078) (INDY:012P).

Kainz et al., "Cytokeratin subunit 19 measured by CYFRA21–1 assay in follow–up of cervical cancer," *Gynecol. Oncol.*, 56:402–405, 1995.

Kelley et al., "Cross–reaction of albumin with polyclonal LH antibody on western blots," *Endo. Res.*, 16(4);477–491, 1990.

Lam et al., "Evaluation of carcinoembryonic antigen, tissue polypeptide antigen, and squamous cell carcinoma antigen in the detection of cervical cancers," *Chinese Med. J.*, 50(1):7–13, 1992.

Lehtovirta et al., "Comparison between squamous cell carcinoma–associated antigen and CA–125 in patients with carcinoma of the cervix," *Gynecol. Oncol.*, 37:276–278, 1990.

(List continued on next page.)

*Primary Examiner*—Charles L. Patterson, Jr.
*Attorney, Agent, or Firm*—Arnold, White & Durkee

[57] ABSTRACT

Disclosed are methods and compositions for identifying, monitoring and treating premalignant and malignant conditions in a human subject. The present invention further discloses methods and compositions for determining cells undergoing apoptosis, and for increasing the efficacy of a cancer therapy. The methods involve the use of apurinic/apyrimidinic endonuclease (APE), independently, as a marker for (pre)malignant conditions and for apoptosis. Also described are polyclonal antibody preparations for use in methods for detecting APE and methods for modulating expression susceptibility of cells to apoptosis.

15 Claims, 21 Drawing Sheets

OTHER PUBLICATIONS

McDicken and Rainey, "The immunohistological demonstration of carcinoembryonic antigen in intra–epithelial and invasive squamous carcinoma of the cervix," *Histopathol.,* 7:475–485, 1983.

Moll et al., "Two distinct mechanisms alter p53 in breast cancer: Mutation and nuclear exclusion," *Proc. Natl. Acad. Sci. USA,* 89:7262–7266, 1992.

Moll et al., "Wild–type p53 protein undergoes cytoplasmic sequestration in undifferentiated neuroblastomas but not in differentiated tumors," *Proc. Natl. Acad. Sci. USA,* 92:4407–4411, 1995.

Nam et al., "Urinary gonadotropin fragment, a new tumor marker," *Gynecol. Oncol.,* 38:66–70, 1990.

Pectasides et al., "Squamous cell carcinoma antigen, tumor–associated trypsin inhibitor, and carcinoembryonic antigen for monitoring cervical cancer," *Am. J. Clin. Oncol.,* 17(4):307–312, 1994.

Robertson et al., "Down–regulation of apurinic/apyrimidinic endonuclease expression is associated with the induction of apoptosis in differentiating myeloid leukemia cells," *Cell Growth Diff.,* 8:443–449, 1997.

Rutanen et al., "Carcinoembryonic antigen in malignant and nonmalignant gynecologic tumors: Circulating levels and tissue localization," *Cancer,* 42:581–590, 1978.

Silber et al., "DNA polymerase β, apurinic/apyrimidinic endonuclease and $O^6$–methylguanine–DNA methyltransferase activity in brain tumors and adjacent normal brain," *Proc. Am. Assoc. Cancer Res. Ann. Mtg,* 36:550, Abstract #3275, 1995.

Stenmark–Askmalm et al., "Cellular accumulation of p53 protein: an independent prognostic factor in stage II breast cancer," *Eur. J. Cancer,* 30A(2):175–180, 1994.

Takahashi and Suzuki, "DNA synthesis–associated nuclear exclusion of p53 in normal human breast epithelial cells in culture," *Oncogene,* 9(1):183–188, 1994.

Toki and Yajima, "Immunohistochemical localization of carcinoembryonic antigen (CEA) in squamous cell carcinoma of the uterine cervix: Prognostic significance of localization pattern of CEA," *Tohoku J. Exp. Med.,* 165:25–32, 1991.

van Nagell et al., "Carcinoembryonic antigen in carcinoma of the uterine cervix: Antigen distribution in primary and metastatic tumors," *Cancer,* 49:379–383, 1982.

Verlooy et al., "Clinical significance of squamous cell carcinoma antigen in cancer of the human uterine cervix," *Gynecol. Obstet. Invest.,* 32:55–58, 1991.

Xu et al., "The apurinic/apyrimidinic endonuclease (APE/ref–1) DNA repair enzyme is elevated in premalignant and malignant cervical cancer," *Anticancer Res.,* 17(5):1–7, 1997.

Yao et al., "Apoptosis in human adenocarcinoma HT29 cells induced by exposure to hypoxia," *J. Nat'l. Cancer Instit.,* 87(2):117–122, 1995.

Zerrahn et al., "Correlation between the conformational phenotype of p53 and its subcellular location," *Oncogene,* 7(7):1371–1381, 1992.

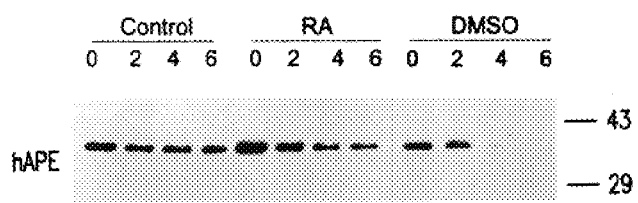
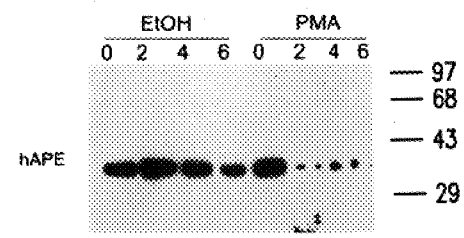
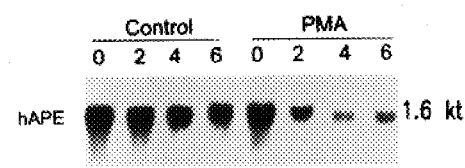
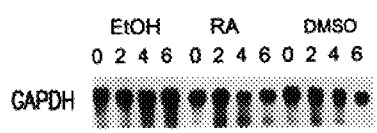
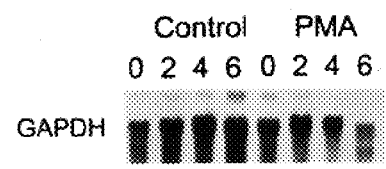
FIG.6A
FIG.6B

```
                          SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
          (A) LENGTH: 1279 base pairs
          (B) TYPE: nucleic acid
          (C) STRANDEDNESS: single
          (D) TOPOLOGY: linear (xi) SEQUENCE DESCRIPTION: SEQ ID NO:1:

GAATTCGGGG GTTGCTCTTT TGCTCATAAG AGGGGCTTCG CTGGCAGTCT GAACGGCAAG      60

CCGGTAAAAA TATTGCTTCG GTGGGTGACG CGGTACAGCT GCCCAAGGGG TTCGTAACGG     120

GAATGCCGAA GCGTGGGAAA AAGGGAGCGG TGGCGGAAGA CGGGGATGAG CTCAGGACAG     180

AGCCAGAGGC CAAGAAGAGT AAGACGGCCG CAAAGAAAAA TGACAAAGAG GCAGCAGGAG     240

AGGGCCCAGC CCTGTATGAG GACCCCCCAG ATCAGAAAAC CTCACCCAGT GCGAAACCTG     300

CCACACTCAA GATCTGCTCT TGGAATGTGG ATGGGCTTCG AGCCTGGATT AAGAAGAAAG     360

GATTAGATTG GGTAAAGGAA GAAGCCCCAG ATATACTGTG CCTTCAAGAG ACCAAATGTT     420

CAGAGAACAA ACTACCAGCT GAACTTCAGG AGCTGCCTGG ACTCTCTCAT CAATACTGGT     480

CAGCTCCTTC GGACAAGGAA GGGTACAGTG GCGTGGGCCT GCTTTCCCGC CAGTGCCCAC     540

TCAAAGTTTC TTACGGCATA GGCGATGAGG AGCATGATCA GGAAGGCCGG GTGATTGTGG     600

CTGAATTTGA CTCGTTTGTG CTGGTAACAG CATATGTACC TAATGCAGGC CGAGGTCTGG     660

TACGACTGGA GTACCGGCAG CGCTGGGATG AAGCCTTTCG CAAGTTCCTG AAGGGCCTGG     720

CTTCCCGAAA GCCCCTTGTG CTGTGTGGAG ACCTCAATGT GGCACATGAA GAAATTGACC     780

TTCGCAACCC CAAGGGGAAC AAAAAGAATG CTGGCTTCAC GCCACAAGAG CGCCAAGGCT     840

TCGGGGAATT ACTGCAGGCT GTGCCACTGG CTGACAGCTT TAGGCACCTC TACCCCAACA     900

CACCCTATGC CTACACCTTT TGGACTTATA TGATGAATGC TCGATCCAAG AATGTTGGTT     960

GGCGCCTTGA TTACTTTTTG TTGTCCCACT CTCTGTTACC TGCATTGTGT GACAGCAAGA    1020

TCCGTTCCAA GGCCCTCGCG AGTGATCACT GTCCTATCAC CCTATACCTA GCACTGTGAC    1080

ACCACCCCTA AATCACTTTG AGCCTGGGAA ATAAGCCCCC TCAACTACCA TTCCTTCTTT    1140

AAACACTCTT CAGAGAAATC TGCATTCTAT TTCTCATGTA TAAAACGAGG AATCCTCCAA    1200

CCAGGCTCCT GTGATAGAGT TCTTTTAAGC CCAAGATTTT TTATTTGAGG GTTTTTTGTT    1260

TTTTAAAAAA CCCGAATTC                                                 1279

(2) INFORMATION FOR SEQ ID NO:2:

(i) SEQUENCE CHARACTERISTICS:
          (A) LENGTH: 318 amino acids
          (B) TYPE: amino acid
          (C) STRANDEDNESS:
          (D) TOPOLOGY: linear
```

(xi) SEQUENCE DESCRIPTION: SEQ ID NO:2:

```
Met Pro Lys Arg Gly Lys Lys Gly Ala Val Ala Glu Asp Gly Asp Glu
 1               5                  10                  15

Leu Arg Thr Glu Pro Glu Ala Lys Lys Ser Lys Thr Ala Ala Lys Lys
                20                  25                  30

Asn Asp Lys Glu Ala Ala Gly Glu Gly Pro Ala Leu Tyr Glu Asp Pro
            35                  40                  45

Pro Asp Gln Lys Thr Ser Pro Ser Ala Lys Pro Ala Thr Leu Lys Ile
        50                  55                  60

Cys Ser Trp Asn Val Asp Gly Leu Arg Ala Trp Ile Lys Lys Lys Gly
 65                  70                  75                  80

Leu Asp Trp Val Lys Glu Glu Ala Pro Asp Ile Leu Cys Leu Gln Glu
                85                  90                  95

Thr Lys Cys Ser Glu Asn Lys Leu Pro Ala Glu Leu Gln Glu Leu Pro
            100                 105                 110

Gly Leu Ser His Gln Tyr Trp Ser Ala Pro Ser Asp Lys Glu Gly Tyr
            115                 120                 125

Ser Gly Val Gly Leu Leu Ser Arg Gln Cys Pro Leu Lys Val Ser Tyr
    130                 135                 140

Gly Ile Gly Asp Glu Glu His Asp Gln Glu Gly Arg Val Ile Val Ala
145                 150                 155                 160

Glu Phe Asp Ser Phe Val Leu Val Thr Ala Tyr Val Pro Asn Ala Gly
                165                 170                 175

Arg Gly Leu Val Arg Leu Glu Tyr Arg Gln Arg Trp Asp Glu Ala Phe
            180                 185                 190

Arg Lys Phe Leu Lys Gly Leu Ala Ser Arg Lys Pro Leu Val Leu Cys
        195                 200                 205

Gly Asp Leu Asn Val Ala His Glu Glu Ile Asp Leu Arg Asn Pro Lys
    210                 215                 220

Gly Asn Lys Lys Asn Ala Gly Phe Thr Pro Gln Glu Arg Gln Gly Phe
225                 230                 235                 240

Gly Glu Leu Leu Gln Ala Val Pro Leu Ala Asp Ser Phe Arg His Leu
                245                 250                 255

Tyr Pro Asn Thr Pro Tyr Ala Tyr Thr Phe Trp Thr Tyr Met Met Asn
            260                 265                 270

Ala Arg Ser Lys Asn Val Gly Trp Arg Leu Asp Tyr Phe Leu Leu Ser
        275                 280                 285

His Ser Leu Leu Pro Ala Leu Cys Asp Ser Lys Ile Arg Ser Lys Ala
    290                 295                 300

Leu Ala Ser Asp His Cys Pro Ile Thr Leu Tyr Leu Ala Leu
305                 310                 315
```

METHODS AND COMPOSITIONS FOR THE USE OF APURINIC/APYRIMIDINIC ENDONUCLEASES

This application in is a continuation-in-part of U.S. Provisional Patent Application No. 60/019,561, filed Jun. 11, 1996 and U.S. Provisional Patent Application No. 60/019, 602, filed Jun. 11, 1996. The entire text of each of the above-referenced disclosures is specifically incorporated by reference herein without disclaimer.

BACKGROUND OF THE INVENTION

A. Field of the Invention

The present invention relates generally to the fields of molecular biology, gene regulation and pathology. More specifically, in certain aspects, the invention relates to the identification of premalignant or malignant conditions in tissues. In other aspects, the invention relates to methods and compositions for the identification of apoptosis, or programmed death, in cells. In particular, the present invention relates to monitoring of levels of apurinic/apyrimidinic endonucleases, also known as APE's.

B. Related Art (i) Cancer Markers

Despite continued efforts worldwide to identify useful prognostic factors for premalignant and malignant conditions (hereinafter together referred to as "(pre)malignant conditions") of human tissues, relatively few markers and associated screens have been discovered which reliably identify (pre)malignant conditions. As one specific example, squamous cell carcinoma of the cervix uteri (SCCC) is the second most common female malignancy, and the leading cause of death by cancer in women worldwide (Mitchell et al., 1995; Burger et al., 1995; Richard et al., 1995). Based on recent estimates, there will be approximately 15,800 new cases of invasive disease, 65,000 cases of carcinoma in situ (CIS; premalignant), and 4800 deaths attributed to SCCC annually in the United States alone (American Cancer Society, 1995). African- and Hispanic-American women and poor Caucasian women were found to have a mortality rate from cervical cancer of more than double that of all Caucasian-American women (Burger et al., 1993; Miller et al., 1993; Davis et al., 1995; Parham et aL 1995), and HIV positive women were diagnosed with CIS at five times the rate of HIV negative women (Wright et al., 1994; Heard et al., 1995).

Cervical cancer arises in the squamous cells lining the cervix tissue. Precancerous lesions are known as CIS, dysplasia, or cervical intraepithelial neoplasia (CIN). Although the development of these cells into invasive carcinoma can take ten to twelve years, in about 10% of patients the development is much more rapid, occurring in less than a year (National Cancer Institute, 1995). Early detection of cervical cancer substantially increases the probability of survival, with both malignant and premalignant conditions being detectable by the so-called Pap smear.

While the Pap smear is relatively widely used, and has had an overall positive impact on women's health, it presents several significant drawbacks. Pap smear sampling must be performed by highly trained clinicians to result in an interpretable, representative sample of the cells lining the cervix (Koss, 1989). As well, a trained cytologist must analyze the morphology of the cells upon microscopic examination (Koss, 1989). Significant human error is attributed to both steps, contributing to high levels of false-negative readings (Koss, 1989; Koss, 1993). A majority of studies estimate the rate of false-negatives at 20%–30%, with various other studies putting this value at 5% to in excess of 50% (Morell et al., 1982). In addition, subsequent to a positive interpretation of a Pap smear, a physician typically biopsies the cervical tissue to confirm the diagnosis and assist in the determination of the stage of the disease and the design of an appropriate treatment regimen. The biopsy sample is analyzed by a pathologist for the presence or absence of (pre)malignant cells and to determine the extent of tumor growth. Human error can also arise in these procedures (Sideri, et al., 1982).

In light of these and other shortcomings of the common Pap smear, researchers have been actively seeking a reliable marker for (pre)malignant states in cervical tissue. A useful marker and associated assay are understood to require a number of attributes. An assay using the marker must consistently detect differences in cancer and noncancer, and exhibit both specificity (few false positives) and sensitivity (few false negatives). Quantitative assays find increased utility over those which are merely qualitative, and cancer marker specific for a particular organ or cell type will be more useful for initial screening purposes, but organ/cell specificity is less important for monitoring previously diagnosed patients.

A number of putative markers for (pre)malignant conditions of the cervix have been identified; however, the markers suggested to date exhibit several shortcomings. For instance, squamous cell carcinoma antigen is a glycoprotein purified from SCCC that has been found to be a marker for cancerous conditions of the cervix (Kato et al., 1982; Kato et al., 1984). This marker was originally called T-4 in a lesser-purified form, and serum SCCA was found to be elevated in 61% of SCCC cases overall, ranging from 30–45% in Stage 1 to 90–100% in Stage 4 (Crombach et al., 1989) (FIGO classification, National Cancer Institute, 1995). In original testing of SCCC as a tissue marker using flow cytometry of vaginal smear cells, 85% of SCCC cases, 80% of severe and 43% of mild to moderate dysplasias and 21% of normal specimens contained cells stained with antibodies to SCCA (Suehiro et al., 1986). This lack of specificity decreases the usefulness of SCCA as a marker, which has also been bolstered by the observation that cytosolic concentration of SCCA in normal cells is twice as high in normal cells than in SCCC cells (Crombach et al., 1989).

Another putative marker for SCCC is carcinoembryonic antigen (CEA). One of the most studied antigens using immunohistochemical analysis for the determination of neoplastic cells in SCCC is CEA. Reports as to the percentage of different dysplastic and neoplastic lesions stained have varied (Toki et al., 1991; Rutenan et al., 1978; van Nagell et al., 1982; Bamford et al., 1983; Bychkov et al., 1983; McDiken et al., 1983; Lindgren et al, 1986; Agarwal et al., 1990). Additional possible markers which have been studied, with varying degrees of success, include proliferating cell nuclear antigen (PCNA) (Raju, 1994; Steinbeck et al., 1995), epithelial membrane antigen (EMA) (Bamford et al., 1983; Sarker et al., 1994), various keratins (Rajur et al., 1988; Auger et al., 1990), Tn antigen (Hamada et al., 1993; Hirao et al., 1993), oncogenes and tumor suppressor genes (Kohier et al., 1989; Tervahauta et al., 1994; Hale et al., 1993; Terzano et al., 1993; Sainz et al., 1993; Tervahauta et al., 1993; Cardillo et al., 1993), and various others (Fuchs et al., 1989; Flint et al., 1988; Costa et a., 1987; Lara et al., 1994; Carico et al., 1993; Harlozinski et al., 1985).

(ii) APE

Apurinic/apyrimidinic endonucleases (hereinafter sometimes referred to as "apurinic endonuclease" or "APE")

catalyze repair of baseless sites in DNA. At least 10,000–20,000 of these sites are generated daily in every human cell as a result of oxidation, spontaneous hydrolysis, and the removal of modified bases by DNA glycosylases (Loeb, 1985, FIG. 15). These baseless sites disrupt transcription and are highly mutagenic if not repaired.

The major human apurinic/apyrinmidinic endonuclease is a 37,000 Dalton protein which has been cloned and shown to complement APE deficient bacteria (Demple et al., 1991). APE has been shown to be identical to Ref-1, a redox factor facilitating the DNA binding of a number of transcription factors, many of which are important in oncogenesis, including Fos, Jun, Myb, and members of the ATF/CREB family (Xanthoudakis et al., 1992). Recently, APE has also been shown to be involved in the negative regulation of transcription of the parathyroid hormone gene by extracellular calcium in vitro (Okazaki et al., 1994). Ape also appears to be a major regulator of p53 activity, acting through protein modification of p53 (Jayaraman et al., 1997)

Besides DNA repair activity, the major human APE repair enzyme has been found to exhibit multiple flnctions, many by in vitro studies. For example, investigators studying Ref-1, a redox regulating transcription factor, discovered that Ref-1 and APE were identical (Xanthoudakis et al., 1992). APE/Ref-1 facilitates the DNA binding characteristics of Jun-Jun homodimers, Fos-Jun heterodimers, HeLa AP-1, and numerous other transcription factors, including Myb, members of the CREB family and nuclear factor-κB (Xanthoudakis et al., 1992).

Immunohistochemistry has been used to examine the subcellular distribution of APE in several different human tissues. The results show that levels vary significantly in different tissues (Duguid et al., 1995). APE expression in skin and intestine was tightly linked to cellular maturation. In most tissues, APE was detected primarily in the nucleus, where the APE staining pattern followed that of chromatin. In hepatocytes and some neurons, however, APE was detected primarily in the cytoplasm.

At this point in time, APE has not been associated with any particular pathologic conditions. Though clearly important to cellular function, specific diseases resulting from aberrations in this protein's function are not known.

SUMMARY OF THE INVENTION

The present invention provides a method for identifying a premalignant or malignant condition in a human subject comprising determining the level of APE in cells from a sample from the human subject, wherein an elevated level of APE, as compared to the APE level in corresponding normal cells, indicates a premalignant or malignant condition in the human subject. As used herein the term "normal cells" means cells of the same tissue type, grown and at the same conditions and at the same cell cycle window and state of differentiation. In particular embodiments, the sample is selected from the group consisting of skin, muscle, facia, brain, prostate, breast, endometrium, lung, pancreas, small intestine, blood cells, liver, testes, ovaries, cervix, colon, skin, stomach, esophagus, spleen, lymph node, bone marrow, kidney, peripheral blood, lymph fluid, ascites, serous fluid, pleural effusion, sputum, cerebrospinal fluid, lacrimal fluid, stool and urine.

In other embodiments, the premalignancy or malignancy is selected from the group consisting of brain, lung, liver, spleen, kidney, lymph node, small intestine, pancreas, blood cells, colon, stomach, breast, endometrium, cervix, prostate, testicle, ovary, skin, head and neck, esophagus, bone marrow and blood tumor cells.

In a particular aspect the determining comprises evaluating APE protein levels. In some aspects, the determining may comprise evaluating APE transcript levels. In other aspects, the evaluating may comprise an inununoassay. In those aspects where APE transcript levels are evaluated the present invention may employ quantitative RT-PCR.

The present invention also provides an polyclonal antibody preparation which reacts immunologically with human APE. In other embodiments, there is provided a monoclonal antibody that reacts immunologically with human APE. The monoclonal antibody may farther comprise a detectable label.

In other embodiments, the present invention provides a method for determining the premalignant or malignant state of a cell comprising determining the level of APE in the cell, wherein an elevated level of APE, as compared to the APE level in a corresponding normal cell, indicates a premalignant or malignant state in the cell.

In particular aspects, the determining comprises the steps of: disrupting the cell; contacting the disrupted cell with an antibody that reacts immunologically with APE; and quantitating the amount of APE bound to the antibody. In certain embodiments the cell may disrupted by detergent lysis, freeze-thaw, sonication, osmotic shock or manual rupture. In various independent embodiments the quantitating may be by ELISA or by RIA.

In other embodiments, the determining comprises the steps of: isolating mRNA from the cell; subjecting the mRNA to reverse transcription to produce cDNA; and quantitating APE cDNA by PCR.

The present invention contemplates a kit for identifying APE levels comprising: a first antibody that binds immunologically to APE; and an agent for detection of APE bound to the first antibody. In particular embodiments, the agent may comprise a second antibody or polyclonal sera that binds immunologically to an epitope of APE other than that bound by the first antibody. In other embodiments, the agent may be a second antibody that binds to the Fc region of the first antibody. In more particular aspects the second antibody comprises a detectable label.

The present invention further provides a method for diagnosis of premalignant or malignant condition in a human subject which comprises: administering to the subject an imaging agent comprising antibodies which react immunologically with APE bound to a label which is detectable by an external scan of the subject; and externally scanning the subject to determine whether there is a localized concentration of the imaging agent. In certain aspects the label may be a radioactive label or may be detectable by an X-ray, positron emission or magnetic resonance imaging scanning of the subject.

Also provided by the present invention is a method for therapeutic treatment of an APE-related premalignant or malignant condition in a human subject comprising administering to the patient an effective therapeutic amount of an agent that reduces the APE activity level in premalignant or malignant cells of the human subject. In particular embodiments the reducing comprises inhibiting expression of an APE gene in the cells. In other embodiments, the reducing comprises inhibiting APE function in the cells. In certain aspects the inhibiting may comprise contacting the cells with antisense APE expression constructs. Alternatively, the inhibiting comprises contacting the cells with antibodies that bind immunologically to APE.

It has now been determined that decreased amounts of APE are present in the cells undergoing and/or likely to undergo apoptosis. This discovery has enabled the use of APE as a marker for apoptosis, to which the present invention is generally addressed. Thus, in one embodiment, the invention provides methods and materials for the specific and sensitive assay of cells to assist in the identification of an apoptotic condition of the cells, and for modulating the apoptotic behavior of cells. The inventive methods and materials are expected to be highly useful in many fields including inter alia in the study and administration of cancer and cancer therapies.

Thus in alternative embodiments, the present invention provides a method for identifying apoptosis in a cell comprising (i) obtaining a sample and (ii) determining the level of APE in the sample, wherein a decreased level of APE, as compared to a normal APE level for a cell of the same type, indicates that the cell is undergoing apoptosis. In particular embodiments, the level is decreased by at least about 50% compared to the control. In other embodiments, the level is decreased by at least about 75% compared to the control. In yet other embodiments, the level is decreased by at least about 90% compared to the control.

In preferred embodiments, the cell is a tumor cell that has been subjected to chemotherapy, radiotherapy or gene therapy. In particular embodiments, the tumor cell is selected from the group consisting of brain, lung, liver, spleen, kidney, lymph node, small intestine, pancreas, blood cells, colon, stomach, breast, endometrium, prostate, cervix, testicle, ovary, skin, head and neck, esophagus, bone marrow and blood tumor cells.

In certain aspects of the present invention the determining comprises evaluating APE protein levels. The determining may comprise evaluating APE transcript levels. Alternatively, the evaluating may comprise an immunoassay or quantitative RT-PCR.

The present invention describes a method for monitoring the efficacy of a cancer therapy comprising (i) administering a therapeutic agent to cancer cells of a subject and (ii) determining the level of APE in a cancer cell from the subject, wherein a decreased level of APE, as compared to the APE level for the cells prior to the administering, indicates that the cell is undergoing apoptosis and the therapy is effective.

In alternative embodiments, the present invention provides a method for determining the apoptotic state of cells in a sample comprising (i) obtaining a sample and (ii) determining the level of APE in cells of the sample, wherein a decreased level of APE, as compared to the APE level in a cell of the same type, indicates that the cells are undergoing apoptosis. In this context, "a cell of the same type" means a treated tumor cell as compared to an untreated tumor cell, or a diseased cell as compared to a normal cell.

In yet another embodiment, there is provided a method for inducing apoptosis in a cell comprising reducing the amount of APE activity in the cell. In particular embodiments, the reducing comprises inhibiting expression of an APE gene in the cell. More particularly, the inhibiting comprises providing to the cell an APE antisense expression construct. In other embodiments, the reducing comprises inhibiting APE function. In certain embodiments the inhibiting may comprise providing to the cell an anti-APE single-chain antibody expression construct. In other embodiments, the inhibiting may comprise providing to the cell an inactive APE fragment, peptide or mimetic that competes with APE for binding to an APE substrate. To the extent that APE has an apoptotic activity an inactive fragment is defined as an APE fragment that does not have such an apoptotic function but retains all other APE-like functions.

The present invention, in an alternative embodiment, describes a method for inhibiting apoptosis in a cell comprising increasing APE activity in the cell. In particular, the increasing may comprise providing to the cell APE, or an active fragment thereof. In one embodiment, the providing comprises contacting the cell with an expression construct encoding APE or an active fragment thereof. In another embodiment, the providing may comprise contacting the cell with a purified APE polypeptide. In certain aspects the cell may be a T-cell infected with a human immunodeficiency virus.

In another inventive aspect, the present invention provides a method for enhancing the sensitivity of a tumor cell to a chemotherapy, a radiotherapy or gene therapy comprising reducing the amount of APE activity in the cell. The reducing may comprise inhibiting expression of an APE gene in the cell. Alternatively, the reducing may comprise inhibiting APE function.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 2E, FIG. 2F, FIG. 2G and FIG. 2H were HeLa, CaSki, SiHa and C33a cells reacted with purified IgG from the preimmune serum at a concentration two times higher than used with the APE antibody. Little, if any, background staining was detected with the preimmune staining. Magnification view of all panels was 40×.

FIG. 3A and FIG. 3E; hematoxylin and eosin staining of normal cervical tissue. FIG. 3B; normal tissue with pre-immune antibody. FIG. 3C and FIG. 3D; Normal tissue stained with APE antibody. There are only a few cells staining in the epithelium of the normal tissue as marked by the arrow. FIG. 3F–FIG. 3I; mild dysplasia (CINI) stained with APE antibody. An increased number of cells are stained between the arrowheads in FIG. 3F. Magnification was 10× for FIG. 3B and FIG. 3C, 20× for FIG. 3A, FIG. 3D–FIG. 3G and 40× for FIG. 3H and FIG. 3I.

FIG. 4A; hematoxylin and eosin staining of CINI tissue with increased number of nuclei and cell density. FIG. 4B; preimmune control. FIG. 4C, normal cervix tissue with APE antibody. Notice the little or lack of staining of the gland marked by the arrow. FIG. 4D; SCC-G3 increased number of cells staining with the APE antibody and increased intensity of staining. FIG. 4E; SCC-G3 close up of FIG. 4D (see arrow). Increased staining that is both nuclear and cytoplasmic and almost every cell in this neoplastic region is staining compared to FIG. 4C and the normal tissue in FIG. 3. FIG. 4F; Increased staining of cells in the base of the columnar cells (arrow; compare to FIG. 4C). Also, increased cell staining density in the overall tissue. Magnification was 10× for FIG. 4B and FIG. 4D, 20× for FIG. 4A, FIG. 4B and FIG. 4F and 40× for FIG. 4C and FIG. 4E.

FIG. 5A. is hematoxylin and eosin (H&E) staining of prostate tissue with normal (open arrows) and cancer (closed arrow). FIG. 5B open arrows designate normal glandular tissue with low level of APE staining and closed arrow is prostate cancer cells. The level of APE is highly elevated in the prostate cancer. FIG. 5C. cancer cells in prostate invading nerve cell (large arrow).

FIG. 6A and FIG. 6B: Expression of APE in HL-60 cells. FIG. 6A, HL-60 cells at 0, 2, 4, and 6 days after treatment with $10_{-5}$ M RA or 1.25% DMSO, Western blot (top) probed with an affinity purified polyclonal rabbit anti-APE antibody which detects the 37,000 Daltons human APE. Northern blots (middle and bottom) probed for the 1.6 Kb APE mRNA and GAPDH transcripts. FIG. 6B, HL-60 cells treated with 100 nM PMA.

FIG. 7A, HL-60-bcl-2 cells at 0, 2, 4, and 6 days after treatment with $10_{-5}$ M RA or 1.25% DMSO, Western blot (top) probed with an affinity purified polyclonal rabbit anti-APE antibody. Northern blots (middle and bottom) probed for the 1.6 Kb APE and GAPDH transcripts. FIG. 7B, HL-60-bcl-2 cells treated with 100 nM PMA.

FIG. 8A), RA (FIG. 8B), DMSO (FIG. 8C), or PMA (FIG. 8D). Error bars indicate the mean standard deviation, and * indicates p value <0.05.

FIG. 9A 50:50 mix of untreated HL-60 cells and HL-60 cells treated with RA for 6 days. FIG. 9B same cells as in FIG. 9A stained with rhodamine-labeled (re) antihuman APE. FIG. 9C same cells as FIG. 9A stained for fragmented DNA using fluorescein labeled (green) and TUNNEL assay. Individual cell identified with arrows display relative APE expression and fragmented DNA in the same cells for comparison.

FIG. 11A At the indicated days after RA treatment, the TUNNEL assay was used to quantitate the percentage of RA-induced cells harboring detectable DNA fragments. FIG. 11B At indicated days RA treatment, DNA fragmentation was quantitated by diphenylamine assay. The ratio of DNA cleavage products to high molecular weight DNA is given as percentage (▲) HL-60 wt; (○) HL-60 Bcl2.

FIG. 18A lower magnification of a section of prostate tissue showing normal (arrowheads) and cancer cells (arrows with tails). FIG. 18B higher magnification of cancer cells from FIG. 18A. Strong nuclear staining in a punctuate manner. FIG. 18C. low power magnification of prostate tissue with cancerous region to lower left (below arrows) and normal cells in upper right region. Distinctive higher levels of APE staining in the cancerous region.

FIG. 19A H&E staining of prostate with cancer cells. FIG. 19B prostate cancer cells demonstrating both nuclear (arrowhead) and cytoplasmic (arrows with tail) staining with APE antibody, both at higher levels than in normal tissue.

DETAILED DESCRIPTION OF THE PREFERRED EMBODIMENTS

Figure 1:
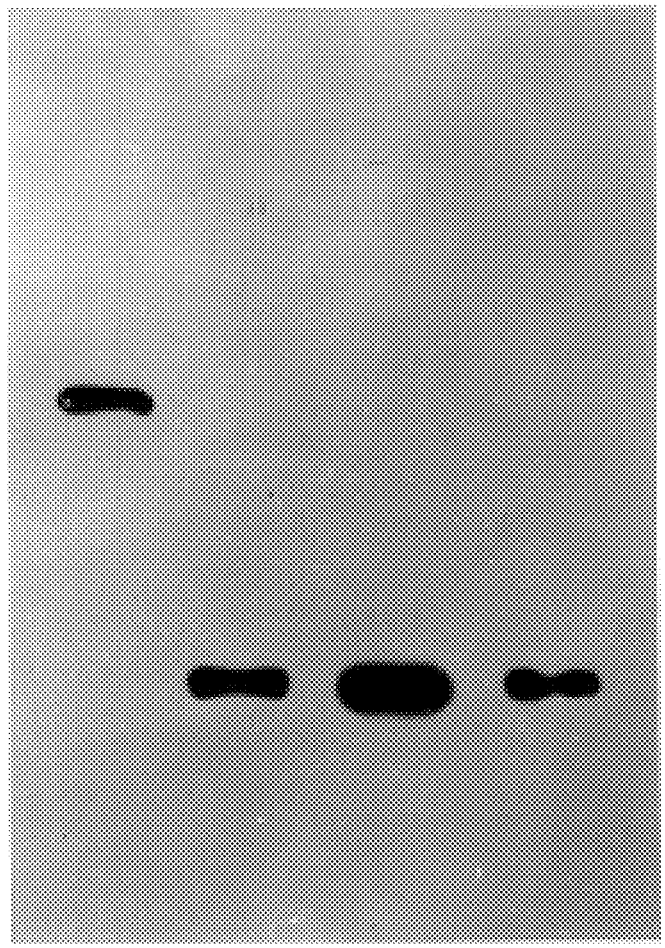
FIG. 1 shows a Western Blot Analysis using affinity purified APE antibody. Total cell extracts (20μg) from the human HPV+ cervical lines CaSki, HeLa and SiHa (lanes 2–4 from left, respectively) were run on a 12% SDS-polyacrylamide gel, blotted to nitrocellulose and reacted with purified antibody to the human APE DNA BER repair enzyme. Only a singe protein band of $M_r$ 37,000 was observed. The first lane contained crude cell extract from E. Coli cells containing the pGET-APE fusion clone. The size of the fuision, overexpressed protein was approximately $M_r$ 63,000, the predicted size (GST=26,000 and APE=37,000).
Figure 2A:
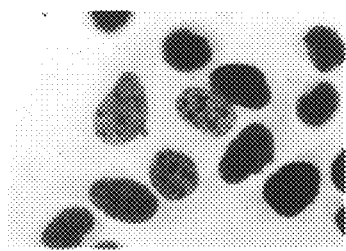
FIG. 2A, FIG. 2B, FIG. 2C, FIG. 2D, FIG. 2E, FIG. 2F, FIG. 2G and FIG. 2H shows APE immunohistochemistry of cervical cancer cell lines. APE antibody staining of HeLa, CaSki, SiHa and C 33a cells is shown in FIG. 2A, FIG. 2B, FIG. 2C and FIG. 2D, respectively. The staining of APE is almost exclusively nuclear.
Figure 2E:
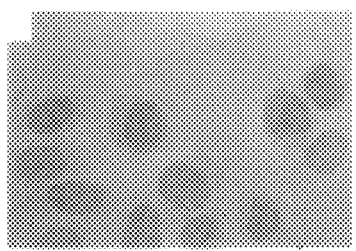
Figure 2B:
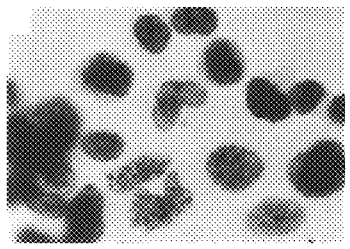
Figure 2F:
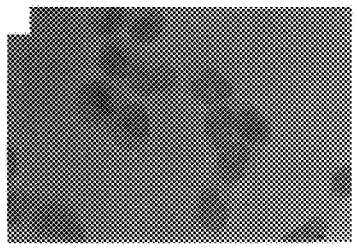
Figure 2C:
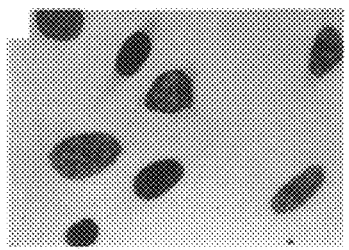
Figure 2G:
Figure 2D:
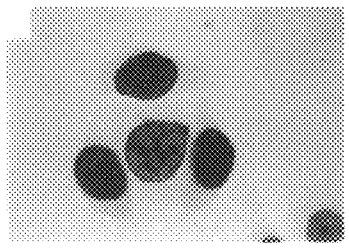
Figure 2H:
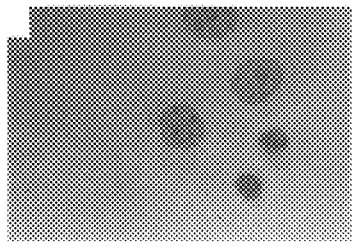
Figure 3A:
FIG. 3A, FIG. 3B, FIG. 3C, FIG. 3D, FIG. 3E, FIG. 3F, FIG. 3G, FIG. 3H and FIG. 3I show immunohistochemical staining of normal and CINI (mild dysplasia) human cervical tissues. Normal tissue has APE staining in nuclei at much lower levels than in the dysplasia tissue. Cells in the CINI tissue have increased levels of APE staining, both in intensity and number of cells staining. This increase is mainly in the nuclei, although some cells have increased APE levels in the cytoplasm as well.
Figure 3E:
Figure 3B:
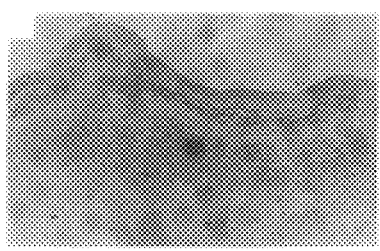
Figure 3F:
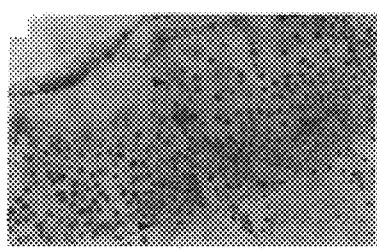
Figure 3C:
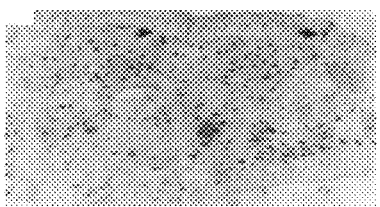
Figure 3G:
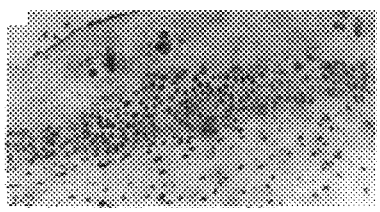
Figure 3D:
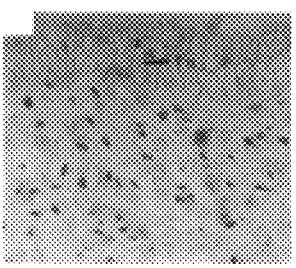
Figure 3H:
Figure 3I:
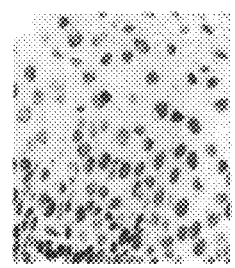

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

I. THE PRESENT INVENTION

The present invention involves the association of APE with (pre)malignant states. Furthermore, the present inventor has discovered that APE can be used as a specific marker for apoptotic conditions in cells. Thus, APE level is an important indicator of the growth status of a cell. These discoveries will be exploited in the diagnosis, treatment and monitoring of malignancies and apoptotic conditions, and are discussed in further detail herein below.

A. APE is Increased in (Pre)malignant States

In the course of studies characterizing a squamous cell carcinoma of the uterine cervix, it was discovered that greater amounts of APE were present in these tumor cells. This observation permits the use of APE as a marker for (pre)malignant conditions in human subjects, to which the present invention is generally addressed. More specifically, it has been discovered that apurinic/apyriridinic endonucleases (APE) can be used as specific markers for premalignant and malignant conditions in humans. Thus, in one embodiment, the present invention provides both methods and devices which facilitate the diagnosis of a (pre) malignant condition in a human subject, which employ APE as a marker for the condition.

In another aspect of the invention, there is contemplated the treatment of APE-related malignancies where abnormally high APE levels not only are indicative of cancer, but are responsible, to some extent, for the malignant phenotype. Thus, by targeting the overexpression of APE and/or APE function in cells with a therapeutic regimen, it will be possible to block or inhibit the abnormally high activity of APE and thereby restore normal growth patterns to the cell. This approach may prove particularly advantageous in combination with other chemo-, radio- or gene-based therapies.

B. APE is Inversely Related to the Apoptotic State

It further has been discovered by the present inventor that apurinic/apyrimidinic endonucleases (APE) can be used as a specific marker for apoptotic conditions in cells. More specifically, the present invention shows that decreased levels of APE are indicative of cells that are undergoing apoptosis. For example, in work to date, the overall levels of APE in blood cells, in particular, cells of lymphoid and myeloid lineage, have been substantially reduced relative to controls as these cells differentiate and apoptose. The present invention may be applied readily to other cell types, including any cells that naturally undergo apoptosis, for example, cells involved in normal or abnormal developmental aging where apoptosis occurs. The present inventor has determined that APE levels decline well before a positive signal is observed using the TUNNEL assay, an assay commonly used to determine apoptosis (Hockenbery, 1995). Thus, methods involving the use of APE to identify cells destined to die via apoptosis constitute an improvement over those currently available.

Thus, in another aspect, the present invention provides methods which facilitate the determination of whether a cell is undergoing apoptosis, using diminution of APE levels as an indicator of this condition. Many cancer chemotherapeutic agents act by inducing cancer cells to undergo apoptosis. Thus, in a particular embodiment, declining levels of APE will be used to identify cells undergoing apoptosis as part of a therapeutic regiment. This will permit one to monitor the efficacy of a treatment and, in certain cases, stop treatment where the effects are or are not seen, thereby avoiding treatment related toxicity.

In yet another aspect, the inventor discloses the possible involvement of APE in the regulation of various topoisomerase II function. Many anticancer drugs "poison" topoisomerase II by enhancing its double-stranded DNA cleavage activity. AP sites are position-specific topoisomerase II poisons (Kingma and Osheroff, 1997). As such, downregulation of APE according to the present invention, in combination conventional topoisomerase II-targeted anticancer drugs, may prove particularly useful against cancers involving topoisomerase II aberrations, and may help overcome multidrug resistance in such cancers.

In still other aspects of the invention, it is expected that the susceptibility of cells to apoptosis may be modulated by increasing, or decreasing the amount of APE enzymatic activity or protein in the cells, to achieve a respective decrease or increase in apoptosis or susceptibility to apoptosis. Thus, further embodiments of the invention relate to such methods for modulating cellular susceptibility to apoptosis. This may be exploited by causing cells to be sensitized to certain classic radio- or chemotherapeutic agents. The decrease or increase in APE activity or protein can be achieved in any suitable fashion, including for example, by action upon the protein per se (e.g., to deactivate the protein), by antibodies or other means, or by action upon transcription or translation of APE, e.g., by antisense oligonucleotides. In this regard, as indicated above, the major APE gene has been cloned and its sequence and location are known. These and other aspects of the present invention are presented in further detail herein below.

In yet another aspect, it may be observed that some cells undergo a premature cell death. These cells, whether responding to an external stress or reacting to an internal genetic abnormality, may nonetheless remain finctional up to their demise. In such cases, it may be advantageous to promote APE such that "normal" APE expression is achieved. This may serve to delay or even prevent apoptosis in these cells.

II. PROTEINS

According to the present invention, APE has been identified as an effective marker for (pre)malignant conditions. The inventor has found that the levels of APE in dysplasia, carcinoma in situ and squamous cell carcinomas of the cervix and the prostate have been substantially elevated relative to controls. This discovery will be exploited in a variety of sampling, prognostic and monitorial strategies in the context of the present invention. In particular embodiments, the present invention isolates APE from a variety of sources in order to make antibodies for use in these strategies.

According to the present invention, APE has been identified as a marker of induction of apoptosis. The inventor has observed an increase in apoptosis in cells having decreased levels of APE. The uses stemming from this observation are manifold, as described above, and will be exploited in the context of the present invention. In one aspect of the invention, therefore, use of the APE protein is contemplated. For example, one may seek to generate antibodies reactive with this molecule for use in certain assays. In other embodiments, one may wish to make functional or nonfunctional variants of this molecule to augment or inhibit APE function in vivo.

Thus, in addition to use of the entire, wild-type APE molecule, the present invention also relates to variants and fragments of the polypeptide that may or may not retain the normal functions of APE. Fragments including the N-terminus of the molecule may be generated by genetic engineering of translation stop sites within the coding region (discussed below). Alternatively, treatment of the APE molecule with proteolytic enzymes, known as protease, can produces a variety of N-terminal, C-terminal and internal fragments. Examples of fragments may include contiguous residues of the APE sequence given in SEQ ID NO:2, of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. The APE Polypeptide Functional Aspects

The major human APE is a known protein of about 37,000 Daltons. The corresponding gene has been cloned and expressed (cDNA sequence deposited in the GenBank data base, Accession No. M80261, as reported in Demple et al., (1991)). APE acts on AP sites in DNA and stimulates the DNA binding activity of Jun-Jun and Fos-Jun dimers, as well as a number of other transcription factors such as NFKB, Myb, AP-1 proteins and members of the ATF/CREB family.

Figure 15A:
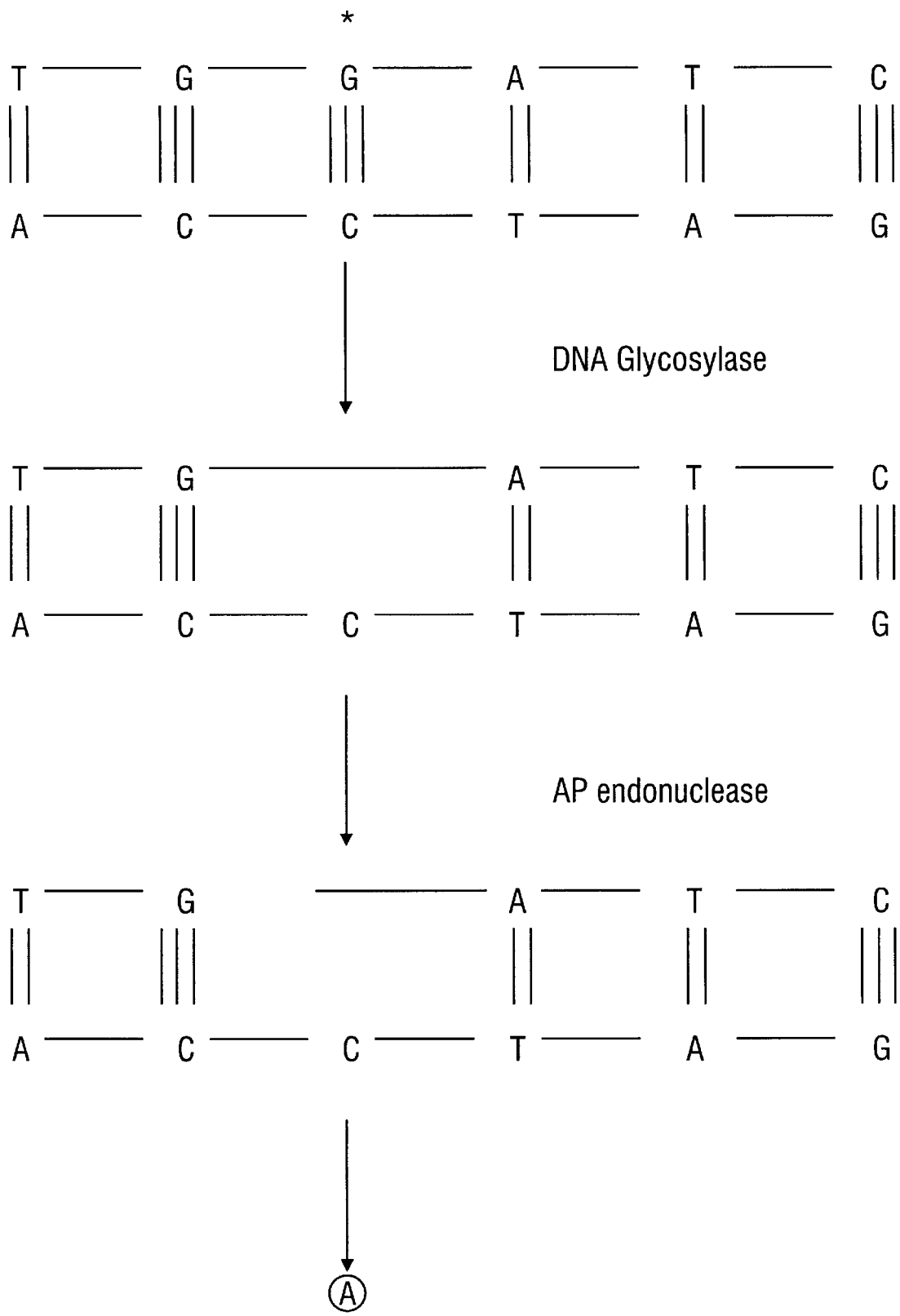
FIG. 15: Schematic of base excision repair (BER) pathway indicating the role of APE in the BER pathway.
Figure 15B:
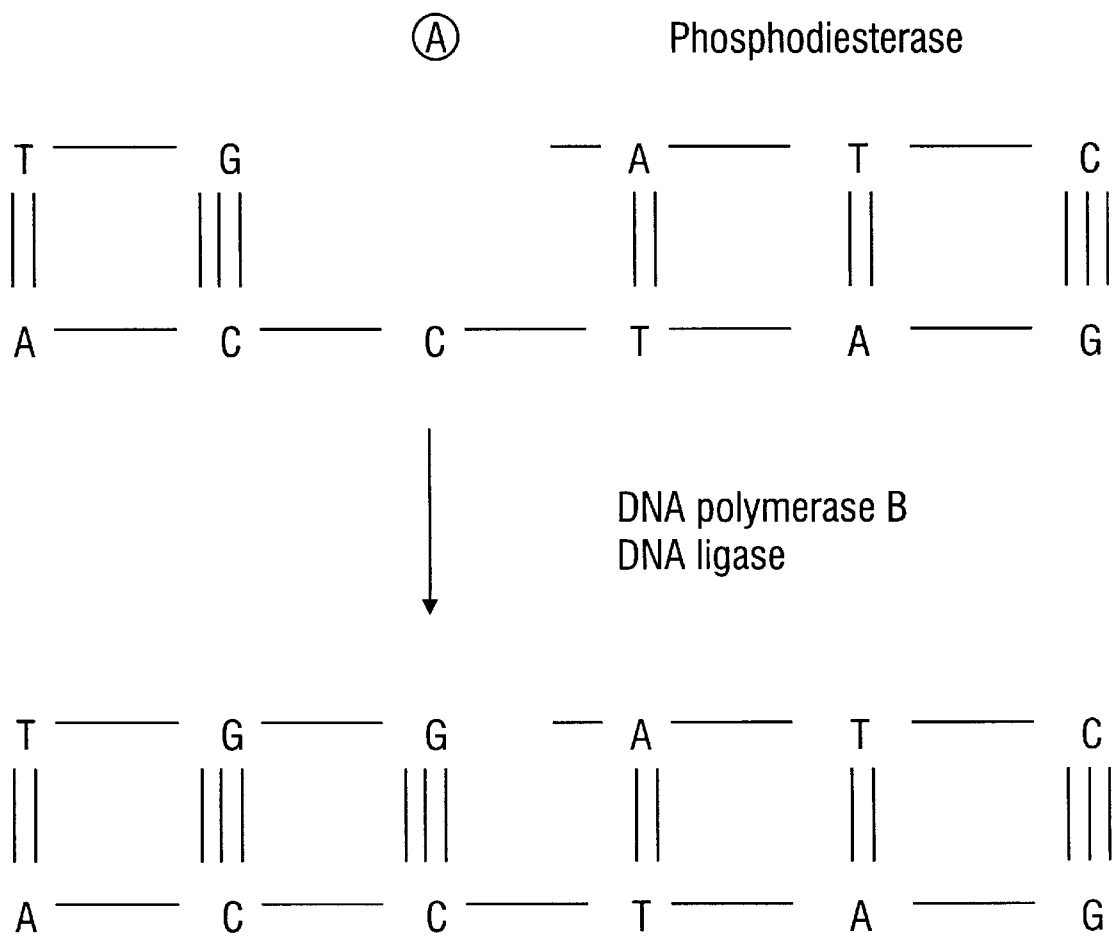

The DNA binding activity of these molecules is sensitive to reduction-oxidation (redox). APE, which is responsible for the major AP-1 redox activity in HeLa cells, represents a novel redox component of the signal transduction processes that regulate eukaryotic gene expression. APE also has been shown to regulate the activity of p53 through a redox mechanism. Since p53 is thought to mediate and control interaction between transcription and DNA repair signaling following genomic damage, APE may also be an important member of this regulatory pathway. Furthermore, redox regulation via APE expression and activity may limit the total amount of functional Fos-Jun complexes and regulate the transformation (cancer promoting) activity of these proteins. Therefore, APE may form a unique link between the DNA base excision repair pathway (FIG. 15), oxidative signaling, transcription factor regulation and cell-cycle control.

The present invention has correlated APE level changes with cancer phenotypes. It is also of interest that APE is also involved in regulating the redox state of various proteins, including transcription factors such as p53 as discussed above. In some human cancers mutations affect the ability of proteins to have their redox status modified by proteins like APE. Hence it may be useful to look at the redox state of APE targets. It may also be advantageous to look at mutations in the redox domain of APE which affect its ability to modulate other proteins. If APE redox activity is destroyed, it doesn't matter if the other downstream proteins, such as p53 or other redox regulated proteins, are mutated or not as they may not be able to be reduced or oxidized due to the APE activity.

B. APE Polypeptide Structural Aspects

Figure 17:
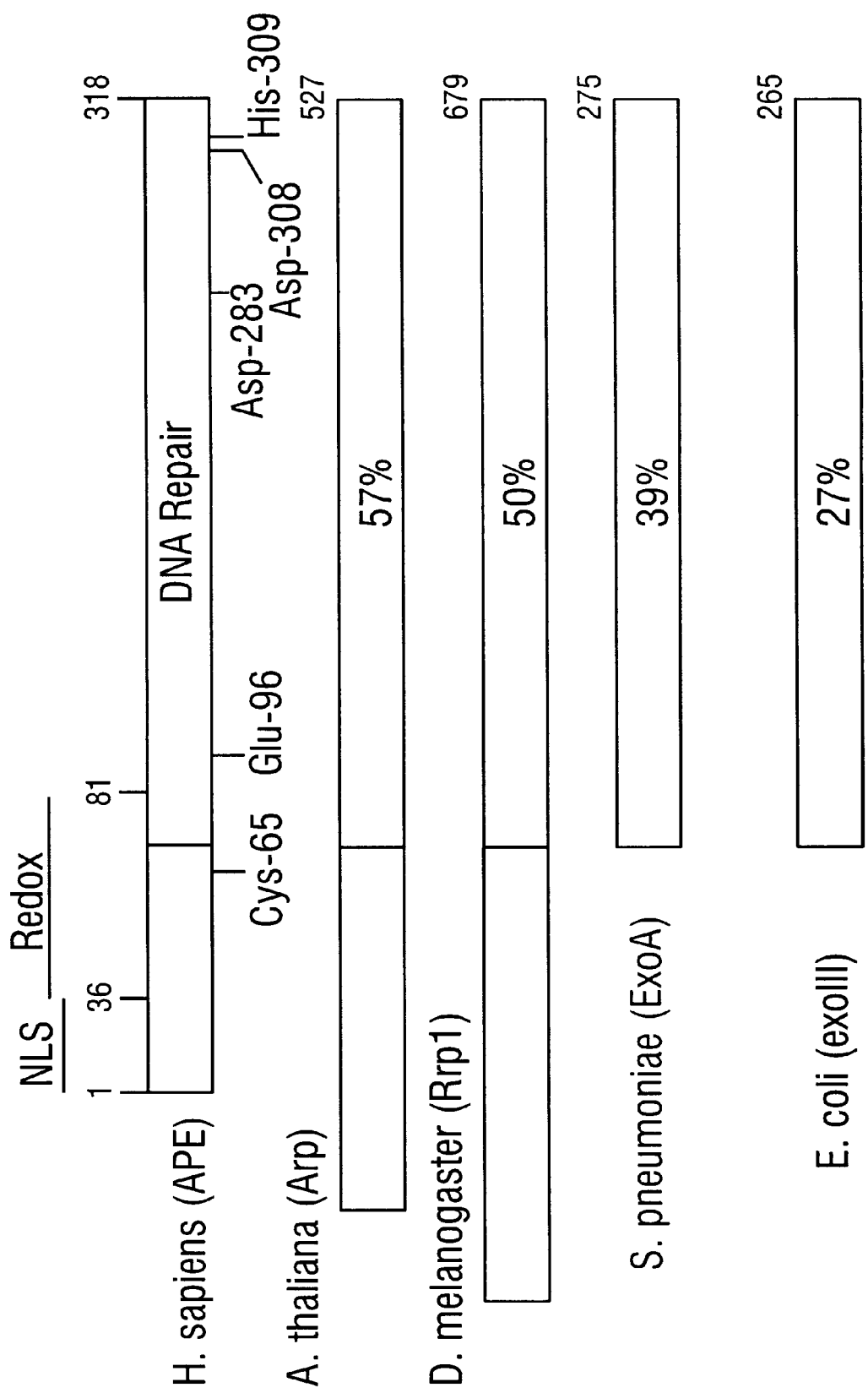
FIG. 17: Illustration of the DNA repair domain of APE. The DNA repair region is located in the carboxy terminal of the protein. Comparison of APE regions of hAPE with APE from A. thaliana (Arp), D. melanogaster (Rip1), S. pneumoniae (ExoA), E. coli (exoIII).

The gene for APE encodes a 318 amino acid polypeptide (SEQ ID NO:2). The predicted molecular weight of this molecule is 37,000 Daltons. The DNA repair domain is located in the carboxy 80% of the protein with amino acids Asp(283), Asp (308) and His (309) being involved in the repair active site. Glu (96) is also important for repair activity (FIG. 17). The redox domain is in the amino portion of the APE protein with Cys(65) being crucial for redox activity (Barzilay, 1995a; Barzilay, 1995b)

As discussed below, the APE gene can be inserted into an appropriate expression system. The gene can be expressed in any number of different recombinant DNA expression systems to generate large amounts of the polypeptide product, which can then be purified and used to vaccinate animals to generate antisera with which further studies may be conducted.

Amino acid sequence variants of the polypeptide may be prepared. These may, for instance, be minor sequence variants of the polypeptide that arise due to natural variation within the population or they may be homologues found in other species. The variations may or may not affect the function of the molecule, and similarly, they may or may not affect the immunological properties of the molecule. Sequence variants can be prepared by standard methods of site-directed mutagenesis such as those described below in the following section.

C. Variants of APE

Amino acid sequence variants of the polypeptide can be substitutional, insertional or deletion variants. Deletion variants lack one or more residues of the native protein which are not essential for function or inunnogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventor that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of APE, but with altered and even improved characteristics.

D. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

E. Purification of Proteins

It will be desirable to purify APE, APE fragments or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "[purification factor]-fold" (e.g. 2-fold, 4-fold, 8-fold, 10-fold, 25-fold, 100-fold or more). The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column or membrane-bound material is synthesized by covalently coupling one of the binding partners to an insoluble matrix or membrane. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Synthetic Peptides

The present invention also describes smaller APE-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

G. Antigen Compositions

As stated above, the present invention provides, in one embodiment, for the use of APE proteins or peptides as antigens for the immunization of animals relating to the production of antibodies. APE, or portions thereof, may be coupled, bonded, bound, conjugated or chemically-linked to one or more agents via linkers, polylinkers or derivatized amino acids. This may be performed such that a bispecific or multivalent composition or vaccine is produced. In a particular embodiment, the antigen composition comprises an APE-fusion protein. The production of antibodies using this composition is described in Example 1 herein below. It is further envisioned that other methods may be used in the preparation of APE antibodies, as will be familiar to those of skill in the art.

III. NUCLEIC ACIDS

As disclosed above, the present invention provides, in one aspect, a DNA sequence encoding an APE protein. In certain aspects, this DNA may be useful in diagnosis of premalignant conditions. In other aspects, this DNA will be useful in the diagnosis of apoptotic conditions. Indeed, nucleic acids are contemplated to be useful for the expression of APE protein, fragments or variants for a variety of diagnostic or therapeutic purposes related independently to (pre) malignant and apoptotic states of a cell. Thus, the present invention also encompasses expression vectors designed to provide for the production of APE. In other aspects, it may be advantageous to decrease the production of APE. This may be accomplished, in one embodiment, by employing antisense APE constructs.

In this regard, as used herein, "DNA sequence" refers to a DNA polymer, in the form of a separate fragment or as a component of a larger DNA construct. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

The gene for the primary human APE has been identified and is known to those of skill in the art. The present invention is not limited in scope to this gene, however, as one of ordinary skill in the could, using the present disclosure, identify and employ homologs from various other species (e.g., rat, rabbit, monkey, gibbon, chimp, ape, baboon, cow, pig, horse, sheep, cat and other species) to achieve the goals outlined herein.

In addition, it should be clear that the present invention is not limited to the specific nucleic acids disclosed herein. As discussed below, an "APE gene" may contain a variety of different bases and yet still produce polypeptides that are structurally and/or functionally indistinguishable, from the human gene disclosed herein.

Similarly, any reference to a nucleic acid should be read as encompassing an expression vector and host cell containing that nucleic acid. In addition to diagnostic considerations, cells expressing nucleic acids of the present invention may prove particularly useful in the context of screening for agents that induce, repress, inhibit, augment, interfere with, block, abrogate, stimulate or enhance the function of the APE polypeptide.

A. Nucleic Acids Encoding APE

The human gene for APE is disclosed in SEQ ID NO:1. Nucleic acids according to the present invention may encode an entire APE gene, a functional domain of an APE gene, or any other fragment of the APE sequence set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

As stated above, it also is contemplated that a given APE from a given species may be represented by natural variants that have slightly different nucleic acid sequences but, nonetheless, encode the same protein (see Table 1 below).

As used in this application, the term "a nucleic acid encoding an APE polypeptide" refers to a nucleic acid molecule that has been isolated free of total cellular nucleic acid. In preferred embodiments, the invention concerns a nucleic acid sequence essentially as set forth in SEQ ID NO:1. The term "as set forth in SEQ ID NO:1" means that the nucleic acid sequence substantially corresponds to a portion of SEQ ID NO:1. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAO | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Theronine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1 will be sequences that are "as set forth in SEQ ID NO:1". Sequences that are essentially the same as those set forth in SEQ ID NO:1 may also be functionally defined as sequences that are capable of hybridizing to a nucleic acid segment containing the complement of SEQ ID NO:1 under standard conditions.

The DNA segments of the present invention include those encoding biologically functional equivalent APE proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

DNA analog sequences are "substantially identical" to the specific DNA sequences disclosed herein if: (a) the DNA analog sequence is derived from substantially the entire coding regions of the native mammalian APE gene; or (b) the DNA analog sequence is comparable in length with and capable of hybridization to DNA sequences of (a) under moderately stringent conditions and which encode biologically active APE molecules; or (c) DNA sequences which are degenerated as a result of the genetic code to the DNA analog sequences defined in (a) or (b) and which encode biologically active APE molecules. Substantially identical analog proteins will be greater than about 80 percent similar to the corresponding sequence of the native protein. Sequences having lesser degrees of similarity but comparable biological activity are considered to be equivalents. In defining nucleic acid sequences, all subject nucleic acid sequences capable of encoding substantially similar amino acid sequences are considered substantially similar to a reference nucleic acid sequence.

B. Oligonucleotide Probes and Primers

Naturally, the present invention also encompasses DNA segments that are complementary, or essentially complementary, to the sequence set forth in SEQ ID NO: 1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein. Such sequences may span the entire coding region or fragments thereof.

Alternatively, the hybridizing segments may be relatively short oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated.

Longer polynucleotides having 250, 500, 1000 bases or longer are contemplated as well. Such polynucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature.

For example, a medium stringency condition could be provided by about 0.1 to 0.25M NaCl at temperatures of about 37° C. to about 55° C., while a low stringency condition could be provided by about 0.15M to about 0.9M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl,3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KC,1, 1.5 $\mu$M $MgCl_2$, at temperatures ranging from approximately 40° C. to about 72° C. Formamide and SDS also may be used to alter the hybridization conditions.

One way of exploiting probes and primers of the present invention is in sitedirected, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

In some cases, it will be desirable to decrease levels of APE, in the therapeutic treatment of cancer cells. In other cases decreases in APE expression will be important, for example, to facilitate an increase in apoptosis or to enhance the efficacy of a conventional therapy. Antisense treatments are one way of accomplishing such a decrease in APE levels and expression. Antisense technology also may be used to "knock-out" function of APE in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementary rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another approach for reducing APE expression is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al, 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

DNAs (coding, antisense, ribozymes) of the invention can be incorporated into viral, plasmid or other vectors and used to transform various mammalian, bacterial or other cell types to achieve expression of the APE protein in the cells. Illustrative mammalian cells include HeLa, endothelial, fibroblast, germ, brain, lung, liver, spleen, kidney, lymph node, small intestine, pancreas, blood cells, colon, stomach, breast, endometrium, cervix, prostate, testicle, ovary, skin, head and neck, esophagus, bone marrow and blood tumor cells.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase, can be used to obtain high-level expression of the coding sequence of interest. In a preferred embodiment, retroviral LTR promoters are employed in conjunction with the present invention. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| ENHANCER/PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |

TABLE 2-continued

ENHANCER/PROMOTER e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon APE Leukemia Virus

TABLE 3

| Element | Inducer |
| --- | --- |
| MT II | Phorbol Ester (TPA) |
|  | Heavy metals |
| MMTV (mouse mammary tumor virus) | Glucocorticoids |
| β-Interferon | poly (rI) X |
|  | poly (rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers.

Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins encoded by independent genes, intracellular or membrane-bound proteins and selectable markers. In this way, expression of several proteins can be simultaneously engineered into a cell with a single construct and a single selectable marker.

(iv) Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (kidgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al, 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10_9$–$10_{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al, 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al, 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

In a particularly preferred embodiment, the present invention employs retroviral vectors for delivery. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro Roux et al, 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al, 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al, 1990). In particular, the present inventor employs retroviral plasmid transfected into the packaging lines GP+E86 and GP+AM12 (Markowitz et al, 1988a; Markowitz et al., 1988b). The helper virus genome of the packaging line is separated onto two plasmids. The packaging signal and 3' LTR have been removed. Construction of these retroviral lines make the generation of recombinant retrovirus uulikely since at least three recombinational events must occur prior to generation of wild type virus.

Other viral vectors may be employed as expression constructs in the present invention. Vectors derived from viruses such as vaccinia virus (Ridgeway, 1988; Baichwal and Sugden, 1986; Coupar et al, 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al, 1988; Horwich et al, 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al, recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al, 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al, 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet ftrther embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment, the transferring a naked DNA expression construct into cells may involve particle bombardment. This method depends on the ability to accelerate DNA-coated microprojectiles to a high velocity allowing them to pierce cell membranes and enter cells without killing them (Klein et al, 1987). Several devices for accelerating small particles have been developed. One such device relies on a high voltage discharge to generate an electrical current, which in turn provides the motive force (Yang et al, 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, ie., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

(v) Use of genes to transform host cells

One embodiment of the foregoing involves the use of gene transfer to inunortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, antimetabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

IV. GENERATING ANTIBODIES REACTIVE WITH THE APE PROTEIN

As stated above, an important aspect of the present invention contemplates production of antibodies that are immunoreactive with an APE protein molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including chickens, rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to APE-related antigen epitopes. Additionally, it is proposed that monoclonal antibodies specific to the particular constructs may be utilized in other useful applications.

In general, both polyclonal and monoclonal antibodies against APE constructs of the present invention may be used in a variety of embodiments. For example, they may be employed in antibody cloning protocols to obtain cDNAs or genes encoding other APE construct. They may also be used in inhibition studies to analyze the effects of APE construct related peptides in cells or animals. Anti-APE construct antibodies will also be useful in immunolocalization studies to analyze the distribution of APE during various cellular events, for example, to determine the cellular or tissue-specific distribution of APE polypeptides under different points in the cell cycle. A particularly useful application of such antibodies is in purifying native or recombinant APE, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its imnuunogenicity. It is often necessary therefore to boost the host inunune system, as may be achieved by coupling a peptide or polypeptide imnmunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified APE protein, polypeptide or peptide or cell expressing high levels of APE. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC 11-X45-GTG 1.7 and S194/5XX0Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

V. DIAGNOSTIC APPLICATIONS.

According to the present invention, the level of APE increases in cells that are in a (pre)malignant state. This stands in direct contrast to other repair enzymes, such as MGMT, MAG, ERCC1, MDR-1, DNA topoisomerase I, DNA topoisomerase IIα a and GSTπ. Codegoni et al. (1997). Thus, APE represents an indicator of cancers such as cervical, brain, lung, liver, spleen, kidney, lymph node, small intestine, pancreas, blood cells, colon, stomach, breast, endometrium, prostate, cervix, testicle, ovary, skin, head and neck, esophagus, bone marrow and blood tumor cells. Thus monitoring levels of APE will provide an indication of the whether the cell is a normal cell or a (pre)malignant cell, allowing early detecting and intervention in (pre)malignant conditions.

In other aspects, the present invention shows that the level of APE declines as cells undergo apoptosis. Thus, APE represents an early indicator of apoptotic activity. There are a variety of reasons one would seek to determine the apoptotic state of a cell. In a preferred embodiment, this information will provide a clinician with feed back on the efficacy of treatment designed to induce apoptosis, e.g., chemo-, radio- or gene therapy for cancer. For example, if a given treatment does not result in a drop in APE levels by a predetermined time, it may be in the patient's interest to cease the treatment. Similarly, if levels of APE drop in response to a given therapy, the apoptotic action of the therapy may be facilitated and no more therapy is needed. In both these scenarios, undesired toxic effects of the therapy may be avoided without loss of benefit.

In another context, it also may be desirable to examine the apoptotic state of a target cell to determine whether normal or abnormal cell aging, senescence and/or death is occurring. For example, the reduction of certain T-cell populations in immunodeficiency diseases may involve induction of apoptotic functions which could be identified, monitored and treated according to the present invention. For example, in a recent study it was suggested that HIV-1 infected individuals display multiple symptoms of redox imbalance consistent with oxidative stress and their lymphocytes are much more prone to undergo apoptosis in vitro. Oxidative stress is a physiological mediator of programmed cell death in lymphocytes and so HIV is an extreme example of what can happen when regulatory safeguards are compromised. Thus the present invention could be used to monitor and treat such individuals.

Thus, it will be desirable examine APE protein levels, APE transcription and at the APE structural gene and regulatory regions. The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

A. Genetic Diagnosis

One embodiment of the instant invention comprises a method for detecting an increase in the expression of APE by looking at the APE transcripts of a cell or the copy number of the gene. Another embodiment of the instant invention comprises a method for detecting reduction in the expression or function of APE by examining at the genes and transcripts of a cell. Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a control reaction or a statistically significant reference group of normal patients. In this way, it is possible to correlate the amount of APE detected with apoptotic states.

In addition to determining levels of APE, it also may prove useful to examine various types of defects. These defect could include deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of APE produced, both by altering the transcription of the gene or in destabilizing or otherwise altering the processing of either the transcript (mRNA) or protein.

A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR-SSCP.

(i) Primers and Probes

The term primer, as defmed herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemilluminiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al, PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: PCR PROTOCOLS: A GUIDE TO METHODS, AND APPLICATIONS, Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the APE gene construct that may then be analyzed by direct sequencing.

(vi) Kit Components

All the essential materials and reagents required for detecting and sequencing APE and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from patients. By determining that the concentration of a specific mRNA species varies, it is shown that the gene encoding the specific mRNA species is differentially expressed.

In PCR, the number of molecules of the amplified target DNA increase by a factor approaching two with every cycle of the reaction until some reagent becomes linmiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

(viii) Chip Technologies

Specifically contemplated by the present inventor are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Antibodies of the present invention can be used in measuring an increase or decrease in APE expression in healthy and diseased tissues, through techniques such as ELISAs and Western blotting. Illustrative assay strategies which can be used to detect APE include, but are not limited to, immunoassays involving the binding of antibodies (polyclonal or monoclonal) to APE in the sample, and the analysis of the sample for bound antibodies. A number of human and other mammalian antibodies to APE are known, and are available either commercially or through techniques well known to the art and industry. Another suitable antibody material can be obtained, for instance, by raising rabbit antibodies against recombinantly-derived APE as generally described in Example 1 below and in (Duguid et al., 1995). Moreover, for this and other aspects of the invention, it will be understood that the APE antibody structure can be genetically manipulated or incorporated in fusion proteins without departing from the invention. Accordingly, antibodies can be used in the present invention in their natural or genetically altered forms.

The use of antibodies of the present invention, in an ELISA assay is contemplated. For example, anti-APE antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for APE that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

Detection of bound antibodies to APE can be accomplished in any suitable fashion, including for example the use of labeled APE antibody which is contacted with the sample under binding conditions. In addition, the sample can be contacted with APE antibody under binding conditions, and then subsequently contacted with a label which specifically binds to APE antibody, e.g., a labeled antigen. In this regard, suitable labels will include chemiluminescent, fluorescent, or radionuclear compounds, microparticles, enzymes, or other labels which are known to be useful for detection.

Another detection strategy which can be used in the invention includes a microsphere agglutination assay (MAA). In such assays, uniformly sized spheres of plastic (e.g., of 30 nanometer to 1 micron in diameter, preferably about 100 to 400 nanometers in diameter) may have finctional groups on their surfaces for covalent attachment of biomolecules. While the use of functional groups is common, it is not always necessary as many biomolecules will adhere to plastic itself. As an example, one partner of a specific binding pair (i.e., antibody or antigen) is attached to the surface of the microspheres. The other partner is placed into solution with the microspheres to initiate the assay, and will act as a bridge between microspheres so as to cause agglutination or "clumping" of the microspheres. The rate of agglutination is directly dependent upon the concentration of the binding pair partner in solution. The level of agglutination can be assayed by light scattering or light absorbence of the sample, wherein the amount of light which passes through the solution is measured either at one point in time or at several points in time to derive a rate of change in the amount of light which gets through. This provides an accurate measure of the level of agglutination of the microspheres since they scatter more light than single (non-agglutinated) microspheres. This measure than then be correlated to the concentration of binding partner in the solution.

Thus, in one strategy, the inventive methods can employ an MAA in which the specific binding pair is an APE antibody (Ab) and APE. In a so-called direct assay, the antibody is bound to the surface of the microparticles, so as to enable the assay of a sample for the amount of APE it contains. The APE sample, which can for instance include a preparation containing contents of a cellular specimen, is added to the microspheres, and the level of APE is determined by light scattering measurements generally as described above.

In an MAA inhibition assay, APE levels may be measured indirectly. For the assay, APE is attached to the surface of the microparticles, and APE Ab is diluted into a second reagent buffer at a fixed concentration. The sample to be assayed for APE level is added to the Ab reagent, so that any APE in the sample binds to the Ab. The microsphere reagent is added to begin the reaction, causing agglutination. The rate of agglutination is thus directly proportional to the amount of Ab and inversely proportional to the amount of APE in the sample.

It will be well understood that other means of testing APE levels are available, including, for instance, those involving testing for an altered level of APE enzymatic activity, or Western blot analysis of APE protein levels in tissues or cells using APE antibody, or assaying the amount of antibody or other APE binding partner which is not bound to a sample, and subtracting from the total amount of antibody or binding partner added.

VI. METHODS FOR SCREENING ACTIVE COMPOUNDS

The present invention also contemplates the use of APE and active fragments, nucleic acids coding therefor, and recombinant cells expressing APE at low and high levels in the screening of compounds for inhibition of APE activity or reducing APE expression. Such compounds would be important in a number of aspects. They would be important in regimens for the treatment of APE-related cancers, whether administered alone or in combination with chemo- and radiotherapeutic regimens in the treatment of cancer. Alternatively, by simply reducing APE, these compounds will be instrumental in initiating programmed cell death. In other instances, it may be desirable to determine if a compound is capable of increasing APE levels, thereby preventing apoptosis in cells which have abnormally low APE activity.

These assays may make use of a variety of different formats and may depend on the kind of "activity" for which the screen is being conducted. Contemplated finctional "read-outs" include alterations in APE expression levels, binding to APE or an APE cofactor, inhibition of APE binding to a substrate, apoptosis, presence or lack of growth, presence or lack of metastasis, presence or lack of cell division, presence or lack of cell migration, presence or lack of soft agar colony formation, presence or lack of contact inhibition, presence or lack of invasiveness, or presence or lack of tumor progression or other malignant phenotype.

In addition to testing of single compounds, it may be useful to test combinations of different compounds, especially known compounds such as chemotherapeutic agents. Other combinations might include a compound plus u.v. or ionizing (alpha, beta or gamma) radiation.

A. Cell-Free Assays

In one embodiment, the invention is to be applied to the screening of compounds that bind to the APE molecule or fragment thereof. The polypeptide or fragment may be either free in solution, fixed to a support, expressed in or on the surface of a cell. Either the polypeptide or the compound may be labeled, thereby permitting a determination of binding.

In another embodiment, the assay may measure the inhibition of binding of APE to a natural or artificial substrate or binding partner. Competitive binding assays can be performed in which one of the agents (APE, binding partner or compound) is labeled. Usually, the polypeptide will be the labeled species. One may measure the amount of free label versus bound label to determine binding or inhibition of binding.

Another technique for high-throughput screening of compounds is described in WO 84/03564. Large numbers of small peptide test compounds are synthesized on a solid substrate, such as plastic pins or some other surface. The peptide test compounds are reacted with APE and washed. Bound polypeptide is detected by various methods.

Purified APE can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the APE active region to a solid phase.

Once identified in this format of assay, it is likely that additional studies designed to elucidate the finctional effects of the agent on APE will be conducted, for example, as described below.

B. Cell-Based Assays

Various cell lines containing wild-type or natural or engineered mutations in APE can be used to study various functional attributes of APE and how a candidate compound affects these attributes. Methods for engineering genetic constructs are described elsewhere in this document. In such assays, the compound would be formulated appropriately, given its biochemical nature, and contacted with a target cell. Depending on the assay, culture may be required. The cell may then be examined by virtue of a number of different physiologic assays. These might include measurement of cell growth, division, contact inhibition, metastasis, soft agar formation or other characteristic. Alternatively, molecular analysis may be performed in which the molecular function or state of APE, or related pathways, may be explored. This may involve assays such as those for protein expression, enzyme function, substrate utilization, phosphorylation states of various molecules including APE, cAMP levels, mRNA expression (including differential display of whole cell or polyA RNA) and others described above.

In particular embodiments, the present invention concerns a method for identifying compounds that will modulate expression of wild-type APE. Useful compounds in this regard will not be limited to those mentioned in the present application. The active compounds may include fragments or parts of naturally-occurring compounds or may be only found as active combinations of known compounds which are otherwise inactive. However, prior to testing of such compounds in humans or animal models, it may be necessary to test a variety of candidates to determine which have potential.

Accordingly, in screening assays to identify pharmaceutical agents which modulate APE expression in cells, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

In these embodiments, the present invention is directed to a method for determining the ability of a candidate substance to decrease the wild-type APE expression of cells and to concomitantly induce apoptosis in said cells, the method including generally the steps of:

(a) obtaining a cell with wild-type APE;

(b) admixing a candidate substance with the cell; and (c) determining the ability of the candidate substance to reduce the APE content of the cell.

To identify a candidate substance as being capable of modulating APE expression, one would measure or determine the APE status of a cell. If that cell has the ability to express APE, its basal APE content in the absence of the added candidate substance is measured. One would then add the candidate substance to the cell and redetermine the wild-type APE in the presence of the candidate substance. A candidate substance which decreases the APE expression relative to the cell's APE expression in the absence of the substance is indicative of a candidate substance with wild-type APE expression inhibiting capability, and will therefor have therapeutic cancer reducing and apoptotic potential as described in the present invention.

Conversely it may be useful to increase the APE level in cells that are undergoing premature cell death or to halt apoptosis, in this regard it will be useful to employ a screening assay that will identify candidate substances that increase or enhance the expression and activity of APE. This screening assay is quite similar to that described above to measure increases in decreases in APE levels. After obtaining an suitable test cell, one will admix a candidate substance with the cell a measure APE levels to determine if increases in APE synthesis or steady state levels have occurred.

"Effective amounts", in certain circumstances, are those amounts effective at reproducibly decreasing APE expression in cells in comparison to their normal levels. Compounds that achieve significant appropriate changes in activity will be used. If desired, a battery of compounds may be screened in vitro to identify other agents for use in the present invention.

C. In Vivo Assays

The present invention also encompasses the use of various animal models. By developing or isolating cell lines that express APE at altered levels or express APE variants, one can generate disease models in various laboratory animals. These models may employ the orthotopic or systemic administration of cells to mimic various disease states. Alternatively, one may APE-related disease states in animals by providing agents known to affect APE levels. Finally, transgenic animals that lack or overexpress a wild-type APE or an altered/mutant APE such as an an APE with the redox region deleted or mutated, may be utilized as models for treatment. Again, animal models provide a useful vehicle for testing combinations of agents as well.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumnoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

D. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for APE or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate a various proteins, selected by a functional assay, and then solve its crystal structure. In principle, this approach yields a pharmacore upon which subsequent drug design can be based. For antibodies, it is possible to bypass 1.-2 protein crystallography by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen. Anti-idiotype approaches may be applied, in theory, to any target binding protein.

VII. THERAPEUTIC APPLICATIONS

The present invention involves, in another embodiment, the treatment of cancer. The types of cancer that may be treated, according to the present invention, is limited only by the involvement of APE. By involvement, it is not even a requirement that APE be mutated or abnormal, but merely that an abnormally high level of APE expression be present. Thus, it is contemplated that a wide variety of tumors may be treated using APE therapy, including cancers of the cervix, prostate, brain (glioblastoma, astrocytoma, oligodendroglioma, ependymomas), liver, kidney, brain, breast, colon, stomach, head & neck, skin, bone marrow, blood, lung, adenocarcinoma, and other tissues.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

The present invention also involves the use of APE, APE genes, APE antibodies APE activity modulation and determination of APE levels in therapeutic settings. The methodologies for effecting these therapies are set forth throughout the specification. The following is an outline of how those of skill in the art would proceed in attaining these therapeutic goals.

A. Genetic Based Therapies

Thus, one of the therapeutic embodiments contemplated by the present invention is the intervention, at the molecular level, in the expression of APE. The present inventor intends to provide to a cell an expression construct capable of increasing or decreasing APE levels that cell. In a particular embodiment, the present invention contempaltes providing to a cell an expression construct capable of providing an antisense APE to said cell. Such a construct will be therapeutically effective as an anticancer agent, which results in a decrease, abrogation or elimination of cancer cell growth or tumor size. In alternative embodiments, such gene based therapies are provided to a cell to increase apoptosis in said cell.

Any nucleic acid encoding an APE protein, as described herein, could be utilized, as could any of the sequence variants discussed above which would encode the same, or a biologically equivalent polypeptide. Different constraints are placed on the use of antisense constructs, which require specific levels of identity to achieve hybridization. The lengthy discussion of expression vectors and the genetic elements employed therein is incorporated into this section by reference. Particularly preferred expression vectors are viral vectors such as adenovirus, adeno-associated virus, herpes virus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any setting, systemic delivery is contemplated. This will prove especially important, for example, in attacking microscopic or metastatic cancer. Where a discrete target cell or tissue site may be identified, a variety of direct, local and regional approaches may be taken. For example, an organ may be directly injected with the expression vector. Also, a tumor bed may be treated prior to, during or after resection. Following resection, one generally will deliver the vector by a catheter left in place following surgery. One may utilize the appropriate surrounding vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way an anti-APE may be utilized according to the present invention.

B. Augmenting Classic Chemo-, Radio- and Genetic Therapies

In another embodiment, the reduction of APE activity levels in tumor cells may augment the response of those cells to other kinds of cancer therapy. The mechanism by which this phenomenon occurs are not well established, but given the role of APE in DNA repair, the loss of this function may well lead to irreparable damage and, hence, apoptosis in affected cells.

Reduction of APE activity may be achieved by one of a variety of different mechanisms. Clearly, if a single compound is available that will specifically reduce APE function, this would be the preferred option. One example of such an agent is an antisense construct that would target APE genes and transcripts, thereby preventing transcription or processing/translation, respectively. Another approach might be the use of antibodies, or corresponding single-chain antibody gene constructs. The former suffers from constraints in importing the rather large (160 Kd) molecule into the cell in a finctional state. Yet another approach would be to provide a peptide or mimetic that would mimic part of the APE molecule such that the peptide or mimetic would effectively compete with APE but not perform APE-like function.

Agents or factors suitable for use in a combined therapy include radiation and waves that induce DNA damage such as, γ-irradiation and X-rays and the like. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

A variety of chemical compounds, also described as "chemotherapeutic agents," function to induce DNA damage, all of which are intended to be of use in the combined treatment methods disclosed herein. For example, agents that directly cross-link nucleic acids, specifically DNA, are envisaged to facilitate DNA damage leading to a synergistic, antineoplastic combination with APE modulation. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mgkg/day being commonly used.

Thus, specific chemotherapeutic agents contemplated to be of used, include, e.g., adriamycin, 5-fluorouracil (5FU), etoposide (VP-16), camptothecin, actinomycin-D, mitomycin C, cisplatin (CDDP) nitrosoureas (BCNU, CNU) and even hydrogen peroxide, MMS, mafosfamide, thiotepa, free radical radiomimetics such as bleomycin, and antimetabolites such as Ara-C. The invention also encompasses the use of a combination of one or more of these agents with radiation-based treatments, such as the use of X-rays, with the further addition of APE down-regulation or inhibition of activity. In certain embodiments, the use of topoisomerase II inhibitors such as VP-16 and camptothecinin in combination with radiation and antisense APE expression are particularly preferred.

In addition to chemo- and radiotherapies, it also is contemplated that combination with gene therapies will be advantageous. For example, p53 or p16 are powerful tumor suppressors that can be used effectively as therapeutics. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf; erb, src, fms, jun, trk, fos, ret, gsp, hst, bcl and abl, using either a sense or antisense approach.

The skilled artisan is directed to "Remington's Pharmaceutical Sciences" 15th Edition, chapter 33, in particular pages 624–652. In this regard, some classes of agents include alkylating agents such as nitrogen mustards, ethylenimines and methylmelamines, alkyl sulfonates, nitrosoureas, triazenes, cyclophosphoramide, and the like; antimetabolites such as folic acid analogues, pyrimidine analogues, in particular fluorouracil and cytosine arabinoside, and purine analogues and the like; natural products such as vinca alkaloids, epipodophyllotoxins, antibiotics, enzymes and biological response modifiers; and miscellaneous products such as platinum coordination complexes, anthracenedione, substituted urea such as hydroxyurea, methyl hydrazine derivatives, adrenocorticoid suppressants and the like. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventor proposes that the regional delivery of APE-inhibitory agents to patients will be a very efficient method for delivering a therapeutically effective gene to counteract the clinical disease. Similarly, the chemo- or radiotherapy may be directed to a particular, affected region of the subjects body. Alternatively, systemic delivery of the APE-regulating compound and/or the secondary agent may be appropriate in certain circumstances.

These compositions all would be provided in a combined amount effective to induce apoptosis in a cell. This process may involve contacting the cells with the APE-related agent(s) and other factor(s) at the same time. This may be achieved by contacting the cell with a single composition or pharmacological formulation that includes both, or by contacting the cell with two distinct compositions or formulations, at the same time, wherein one composition includes the expression construct and the other includes the agent.

Alternatively, the anti-APE therapy treatment may precede or follow the other agent treatment by intervals ranging from minutes to weeks. In embodiments where the other agent and anti-APE therapy are applied separately to the cell, one would generally ensure that a significant period of time did not expire between the time of each delivery, such that the agents would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the anti-APE or the other agent will be desired. Various combinations may be employed, where anti-APE is "A" and the other agent is "B", as exemplified below:

| A/B/A   | B/A/B   | B/B/A  | A/A/B  | B/A/A  | A/B/B  | B/B/B/A | B/B/A/B |
| A/A/B/B | A/B/A/B | A/B/B/A | B/B/A/A | B/A/B/A | B/A/A/B | B/B/B/A |         |
| A/A/A/B | B/A/A/A | A/B/A/A | A/A/B/A | A/B/B/B | B/A/B/B | B/B/A/B |         |

Other combinations are contemplated. Again, to achieve induction of programmed cell death, both agents are delivered to a cell in a combined amount effective to induce apoptosis.

C. Reestablishing Normal APE Levels in APE-Deficient Cells

In other embodiments, the present invention provides a method for treating cells to prevent or render the cells less susceptible to apoptosis, which involves the step of increasing the amount of APE activity or protein in the cells. This may be particularly useful in reestablishing normal APE levels in cells that have normal or abnormal cell senescence and/or death is occurring. For example, the reduction of certain T-cell populations in immunodeficiency diseases are thought to involve apoptotic fuinctions and many of these apoptotic events may be abrogated by the present invention. Similarly, IFNβ overproduction is thought to render circulating memory T cells competent to apoptosis by upregulating the cascade of metabolic events leading to programmed cell death.

The present invention may be able to circumvent such premature cell death that is associated with various immunodeficiencies by supplying a finctional APE. This may be achieved by, for instance, by selective activation or overexpression of an APE gene in the cell which expresses APE. In the alternative, it may be possible to use genetic therapy with APE-expressing vectors, described above, to increase levels of APE is such cells.

D. Monitoring Cancer Therapies

As demonstrated in the Examples (below), the level of APE drops in cells that are preparing to undergo apoptosis. One scenario in which cells are undergoing programmed cell death is as part of a cancer therapy. Thus, the present invention contemplates use of the above-described diagnostic methodologies to measure the efficacy of standard cancer therapies by virtue of a related drop in APE level.

The cancer to be treated may be virtually any type of cancer including cancers of the brain, lung, prostate, cervix, liver, spleen, kidney, lymph node, small intestine, pancreas, blood cells, colon, stomach, breast, endometrium, testicle, ovary, skin, head and neck, esophagus, bone marrow and blood. While some malignancies may exhibit an increase in APE levels, it is not necessary that the cancer exhibit increased APE levels in order for the monitoring to have value.

In one embodiment, the clinician would take a sample of the tumor tissue prior to exposure of the patient to the therapy. A determination of APE levels would provide a base-line for measurement of that tissue's existing APE expression. It also is contemplated that "normal" levels for the corresponding normal tissue would be known by virtue of measuring that tissue type from a statistically significant group of individuals. Thus, both absolute and relative base-lines would be available.

During a therapeutic regimen, additional samples would be taken to determine the effect of the therapy on the APE levels in the tumor and, hence, the likelihood that apoptosis was induced. Based on the type and location of the tumor, the type and duration of treatment, and the health state of the patient, the sampling will vary.

E. Immunotherapies

Immunotherapeutics, generally, rely on the use of immune effector cells and molecules to target and destroy abnormal cells. The immune effector may be, for example, an antibody specific for some marker on the surface of a cancer cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, it is unlikely that APE could serve as a target for an immune effector given that it is unlikely to be expressed on the surface of the cell. However, it is possible that APE may be targeted by immunotherapy using antibodies modified to be taken up by target cells or by a single-chain antibody expression construct.

F. Protein Therapy

Another therapy approach is the provision, to a subject, of an APE polypeptide, active or inactive APE fragment, APE synthetic peptide, APE mimetic or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations. Targeting moieties also may be included in the preparations to aid in the targeting of particular cells and in the uptake of the protein by the target cells.

G. Formulations and Routes for Administration to Patients

Where clinical applications are contemplated, it will be necessary to prepare pharmaceutical compositions— expression vectors, virus stocks, proteins, antibodies and drugs—in a form appropriate for the intended application. Generally, this will entail preparing compositions that are essentially free of pyrogens, as well as other impurities that could be harmful to humans or animals.

The agents can be administered orally, intravenously, intramuscularly, intrapleurally or intraperitoneally at doses based on the body weight and degree of disease progression of the patient, and may be given in one, two or even four daily administrations.

One will generally desire to employ appropriate salts and buffers to render agents stable and allow for uptake by target cells. Aqueous compositions of the present invention comprise an effective amount of the agent, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freezedrying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VIII. EXAMPLES

The following examples are included to demonstrate preferred embodiments of the invention. It should be appreciated by those of skill in the art that the techniques disclosed in the examples which follow represent techniques discovered by the inventor to function well within the practice of the invention, and thus can be considered to constitute preferred modes for of practice. However, those of skill in the art should, in light of the present disclosure, appreciate that many changes can be made in the specific embodiments which are disclosed and still obtain a like or similar result without departing from the spirit and scope of the invention.

Example 1

Materials And Methods

Antibody production: For overexpression of glutathione S-transferase:human APE fusion protein (GST-APE), bacterial cultures (10 ml) containing the human GST-APE fusion constructs were grown overnight at 37° C. in LB plus 100 $\mu g/\mu l$ ampicillin, generally as described previously for other DNA repair genes (Wilson et al., 1996; 1994). Overnight cultures were diluted 1 to 10 in fresh, pre-warmed (37° C.) LB medium supplemented with ampicillin and grown for 1 hour at 37° C. with shaking. Expression of the GST-APE fusion protein was induced by adding isopropyl-$\beta$-D-thiogalactoside (IPTG) to a final concentration of 0.1 mM and growing the cells for an additional 3.5 hours at 37° C. Cells were harvested by centrifugation at 1000×g for 10 minutes and washed once with PBS, pH 7.4. Packed cells were resuspended in 3 ml of PBS and lysed by mild sonication (two 20-second bursts) on ice. The human APE fusion protein was totally soluble. Cellular debris was pelleted by centrifugation at 8500×g for 10 minutes at 4° C. and the supernatant collected containing the soluble human APE fusion protein. The soluble fraction had Triton X-100 added to a final concentration of 0.1% and loaded onto a glutathione Sepharose 4B column, pre-equilibrated with PBS.

Binding of the GST-APE protein was carried out for 3 hours on a nutator at 4° C. The column was subsequently washed with 20 column volumes of PBS containing 0.1% Triton X-100. Following the wash, the fusion protein was eluted with 50 mM Tris, pH 7.5, containing 10 mM glutathione, fractions collected and analyzed by SDS-polyacrylamide gel electrophoresis. This column purified protein was cleaved from the glutathione-S-transferase portion using Factor Xa. The clipped, gel purified proteins were used as antigen for polyclonal antibody production in rabbits and for preabsorbing the antibodies to confin specificity in immunohistochemistry or Western blot experiments.

SDS-Polyacrylamide Gel Electrophoresis, Antibody Production, Electroelution of Protein from Gels and Western Blot Analysis: Protein samples were fractionated on a 12% SDS-polyacrylamide gel. For isolation of gel-purified antigen, column purified GST-APE fusion protein was first cleaved with Factor Xa and the products resolved on a 12% SDS-polyacrylamide gel. The clipped APE protein was excised from the gel and this gel strip placed into dialysis tubing with 1 ml of 1× SDS electrophoresis buffer (0.125 M Tris-HCl; 0.96 M glycine; 0.5% SDS). The tubing was sealed and the antigen eluted in 1× SDS electrophoresis buffer at 150 V for 20 min. This protein was used for both antigen production and immunoabsorption experiments.

In particular, the anti-human apurinic/apyrimidinic endonuclease antibody, anti-APE, was obtained by injection of rabbits with about 15 mg of each (native and denatured) purified GST-APE fusion protein preparation (Harlow and Lane, 1988). Animals were initially injected with the antigen in an emulsion containing equal volume of Hunter's Titer-Max. Preimmune serum was collected at the time of the first injection using the ear bleed method. Red blood cells were removed from the serum by incubation at 4° C. overnight and centrifugation at 3000×g for 10 minutes. Serum (the supernatant) was stored in aliquots at −20° C. Rabbits were anesthetized prior to injections and bleeds with ketamine (35 mg/kg) and rompun (5 mg/kg). Animals were boosted every 3 to 5 weeks with an emulsion containing an equal volume of antigen and incomplete Freund's adjuvant. At this time, anti-APE serum was harvested (5 ml of blood/1b).

For affinity purification of anti-APE, approximately 5 mg of purified GST-APE fusion was electrophoresed on a 12% SDS-polyacrylamide gel and blotted onto a nitrocellulose membrane. The region of nitrocellulose which corresponded to the location of the fusion protein was cut into a strip and used to affinity purify the antibody (Harlow and Lane, 1988; Maniatis et al., 1989). The filter strip was blocked with Blotto for 1 hour at room temperature and incubated with 3 ml of anti-APE serum on a rotator at 4° C. overnight. The filter was washed 3 times with 2× TBST for 10 minutes each. To elute the antibody, the strip was covered in a minimal volume of Elution Buffer (Pierce), placed in a damp chamber and incubated for 20 minutes on the rotator at room temperature. The Elution Buffer was passed over the strip several times and transferred to a labeled tube for storage at 4° C. The sample was subsequently dialyzed against PBS, pH 7.4 for 18 hours and termed affinity purified anti-APE.

Figure 16A:
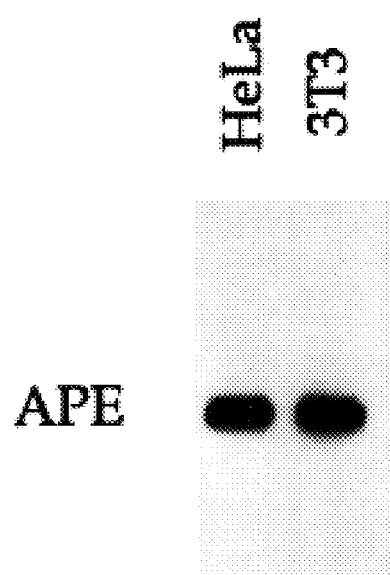
FIG. 16: Polyclonal antibody produced in rabbit or chicken to the human APE protein. Western blot analysis of HeLa cell (human) or NIH3T3 (mouse) cells using antibody produced in rabbits or chickens. The antibodies were affinity purified and only a single cross-reacting protein is visible in the human or mouse cells.
Figure 16B:
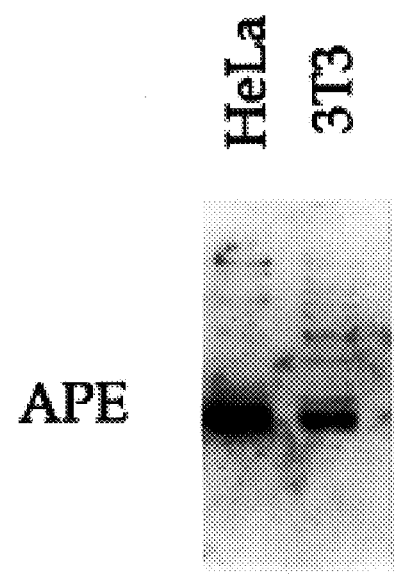

Western blot analysis was performed as has been previously described (Wilson et al., 1994; 1995, FIG. 16). Whole cell extracts were electrophoresed on a 12% SDS-PAGE and electroblotted onto 0.2 micron nitrocellulose. The filter was incubated in blocking buffer which contains 5% non-fat milk for 1 hour. Next, the antibody (affinity purified APE) was diluted to the appropriate concentration (1:100) and incubated with the filter overnight at 4° C. The filter was washed in 1× TBST and incubated in TBST containing 5% milk and cross-reacting proteins were detected using the Chemiluminescence Western Blotting Kit from Boehringer-Mannheim (Indianapolis, Ind.) as directed. Western blot analysis of HeLa cell (human) or NIH3T3 (mouse) cells using antibody produced in rabbits or chickens are shown in FIG. 16. The antibodies were affinity purified and only a single cross-reacting protein is visible in the human or mouse cells.

Figure 20:
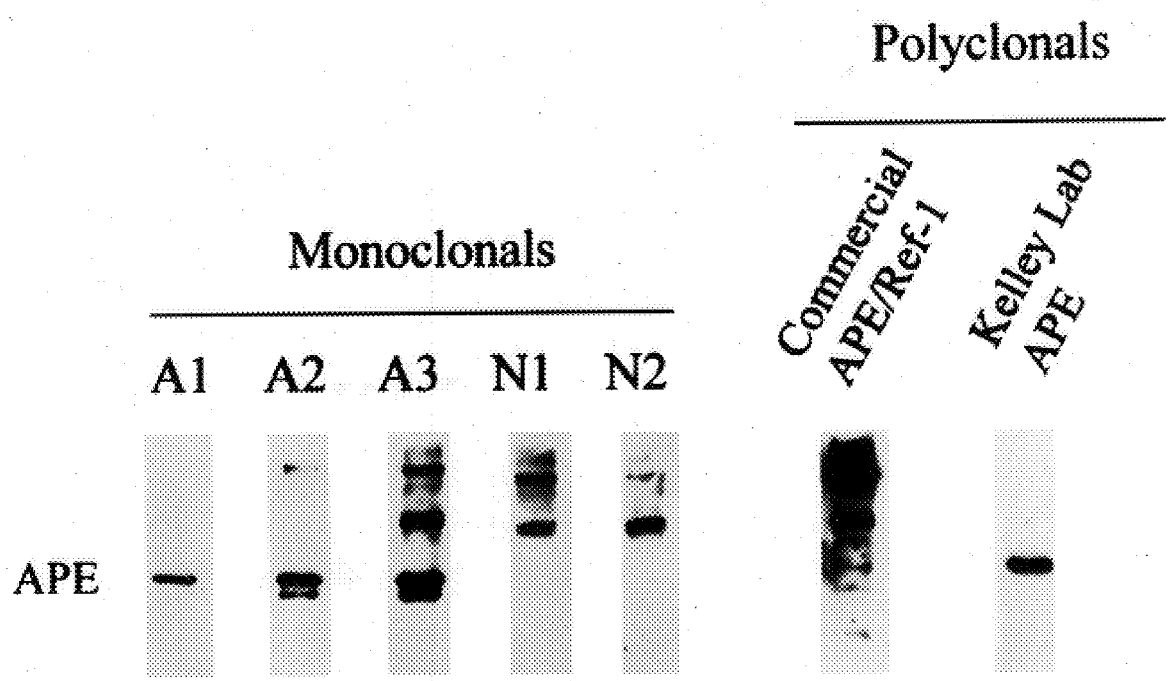
FIG. 20. A comparison of the efficacy of the present APE polyclonal to a commercially available polyclonal and five monoclonal antibodies that have not yet been published.

The inventor has compared the efficacy of the APE polyclonal made herein to a commercially available polyclonal and five monoclonal antibodies that have not yet been published. Using Western blot analysis (FIG. 20), the inventor's APE antibody gives much more specific cross-reactivity to APE protein in HeLa cells compared to the commercially available antibody, i.e., only one cross-reacting band observed. Of the five monoclonal antibodies, only A1 gives a clean signal upon Western blot analysis. Furthermore, the given monoclonal antibodies do not give a detectable signal when used in immunohistochemistry assays and the commercial APE polyclonal does not give a clean signal in IHC. The inventor would be reluctant to use the commercial antibody due to its obvious cross-reactivity to multiple bands as evidenced upon Western blot analysis (FIG. 20).

Example 2

Biopsy Samples

Paraffin-embedded biopsies from over thirty cases of squamous cell carcinoma in situ and squamous cell carcinoma of the cervix were obtained from the archives of University Hospital and Wishard Memorial Hospital, Indianapolis, Ind. This study was approved by the Indiana University Institutional Review Board. Six micron sections were stained with rabbit anti-APE as described above and in (Duguid et al., 1995). Cervical tissue was obtained which had been previously evaluated for cervical cancer or normal controls. The tissues were classified as normal, dysplastic (mild, moderate, severe), cervical intraepithelial neoplasia (CIN) or SCC grade 2 (SCC-G2) or grade 3 (SCC-G3). All samples were analyzed using a blind coding system, such that the antibody staining was performed on numbered slides and the sample diagnosis was not known at the time of processing. Although only representative data are presented in FIGS. 3 and 4, the results have been confirmed with over thirty other cervical cancer tissue samples. Immunohistochemical analysis was performed as previously described (Wilson et al., 1995; Duguid et al., 1995). Briefly, primary anti-APE antibody (rabbit anti-human APE polyclonal) was incubated with the section overnight at 4° C. at a 1:50 dilution in 10% goat serum in PBS. The following day, the sections were washed three times for 5 minutes in PBS followed by incubation with the secondary antibody (biotinylated goat anti-rabbit IgG, Vector Labs, Burlingame, CA) at 15 $\mu$g/ml in 10% goat serum for 1 hour. Following two 5 minute PBS washes, the sections were incubated with aviden and biotinylated horseradish peroxidase complex (ABC elite kit, Vector Labs) for 45 minutes. The sections were then incubated with the chromogen diaminobenzidine (Vector Labs). After development of signal, the sections were washed briefly in $dH_2O$ and dehydrated through a graded alcohol series to xylene, coverslipped, analyzed and photographed. To control for antibody specificity, preimmune IgG was used as the primary antibody in place of the anti-APE antibody at a concentration of 50 $\mu$g/ml. for histological staining, the adjacent sections were stained with hematoxylin and esoin and coverslipped (Duguid et al., 1995; Wilson et al., 1995).

The subcellular distribution and level of APE was examined in thirty biopsies of various stages of cervical cancer, including mild to severe dysplasia, carcinoma in situ and squamous cell carcinoma using immunohistochemistry, and it was found that in all cases of premalignant and malignant tissue, increased levels of APE were detected compared to normal control tissues (FIG. 3).

The specificity of the APE antibody on cervical cell line extracts was confirmed using Western blot analysis of three HIV+ cervical cell lines (CaSki, HeLa and SiHa) (FIG. 1). A single cross-reacting band at Mr 37,000 was observed as expected. The specificity of the APE antibody was also confirmed as it detected the GST-APE fusion protein from E. coli extract of the recombinant overproducing strain. The applicants have found only a single cross-reacting band found in the C33a cell line which is HPV-, but has mutated p53 and retinoblastoma genes. HeLa contains HPV-18, SiHa contains HIV-16 (102 copies/cell) and CaSki also contains HPV-16, but with approximately 600 copies per cell. Since a full 85% of patients with cervical cancers are PHV positive, these cell lines were chosen as representative models of this phenomena (Park et al., 1995; Schiffman et al., 1995). The HPV- C33a cell line was an initial attempt to determine if there was any relationship to APE expression levels and HPV. No relationship has been observed in work to date.

The subcellular location of APE in cervical cancer cell lines was determined and compared with the actual human cervical tissues. The APE antibody predominantly demonstrated cross-reactivity in the nuclei of the four cell lines (FIG. 2). There did not appear to be much detection of protein in the cytoplasm of the cells, nor was there any immediately observable differences between the three HPV+ (HeLa, CaSki and SiHa) and HPV- (C33a) cell lines. A rather distinctive punctate staining of the nucleus was observed. The nuclear localization was confirmed using human normal and cervical tissues and is presented below.

The subcellular distribution of APE was examined in a variety of cervical tissues, spanning the range of cervical cancer progression, including normal controls, mild to severe dysplasia, CIN, and SCC-G2 and SCC-G3. Representative immunohistochemical stainings of some of these normal and cervical cancer conditions are shown in. FIGS. 3 and 4. The level of APE protein is consistently increased compared to normal cervical tissue, beginning with the mild dysplasia and dramatically elevated in the SCC-G2 and SCC-G3 (FIG. 3). Although immunohistochemistry is not as quantitative as other types of analysis such as Western blotting of proteins or in situ hybridization for mRNA levels, it can be used for comparative analysis.

Figure 4A:
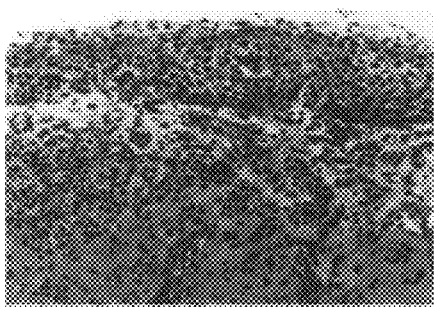
FIG. 4A, FIG. 4B, FIG. 4C, FIG. 4D, FIG. 4E and FIG. 4F shows an immunohistochemical staining of SCC-G2 and SCC-G3 with human APE antibody. In the SCC tissues, the antibody staining is dramatically increased, both in intensity and numbers of cells staining.
Figure 4D:
Figure 4B:
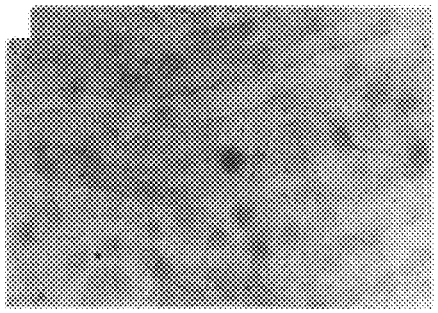
Figure 4E:
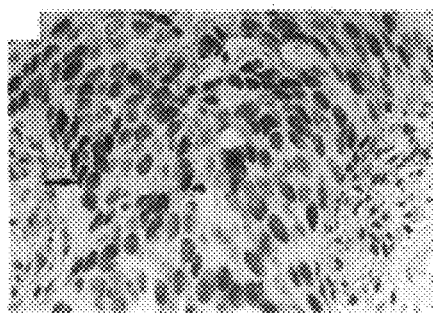
Figure 4C:
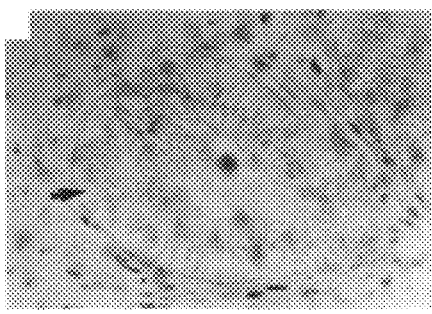
Figure 4F:

The increase in the APE protein appears to be mainly nuclear; however, upon close examination of a large number of samples, there also appears to be an increase in the level of APE that is both nuclear and cytoplasmic in some cells (FIG. 4E). This may just be an overall increase in APE protein expression or it may be the result of a decrease in trafficking into the nucleus.

Example 3

Cervical Cancer Evaluation for APE Staining

Table 4 depicts cervical cancer evaluation data. Two aspects of the staining were scored. First, an estimation of the proportion of cells staining and the intensity of the nuclear staining from 0 to 3. Any cells staining less than 10% of the cells positive was considered negative (0).

First, the immunostain was looked at, various different patterns of staining were selected, up to three, and then correlated these areas with the H&E stain. Interpretation of these specific areas without knowing what the case actually signed out was determined. On each slide, there may be up to three diagnosis (Dx), followed by the stain interpretation for that specific area.

Regions of the epithelium staining were basal layer (BL), Basilar 1/2 (B1/2) and Superficial 1/2 (S1/2). these regions do not apply with the invasive squamous cell lesions.

There were only a few discrepancies in the interpretation versus the sign out, but no significant difference. Further, staining followed pathology and APE staining appears to be more predictive and a marker of earlier stages in dysplasia and CINI, etc. and not as much on the very full blown SCCC. Therefore it may be a much better marker for earlier and premalignant stages of cervical cancer.

TABLE 4

| Pathology Diagnosis | Number of Cases | APE Ab Diagnosis* |
|---|---|---|
| CIN 1 | 13 | 12-CIN 1; 1-CIN 3 |
| CIN 2 | 10 | 8-CIN 2; 2-CIN 1 |
| CIN 3 | 7 | 4-CIN 3; 3-CIN 2 |
| SCC G1 | 3 | 3-CIN 3 |
| SCC G2 | 7 | 5-SCC G2; 2-CIN 3 |
| SCC G3 | 5 | 5-SCC G3 |
| Normal | 10 | 10 Normal, low level of staining |
| Total | 55 | |

The actual staging differed in some cases, but this assumes the pathology grading was accurate. No cases went undetected.

Example 4

APE in Prostate Cancer Tissue

Cancerous prostate tissue was stained in accordance with the protocols described above for the cervical tissue. The results, discussed above and presented in FIG. 5A–C as well as FIG. 18A–C and FIG. 19A and FIG. 19B demonstrate that elevated levels of APE are also an indicator for cancerous prostate tissue.

Figure 5A:
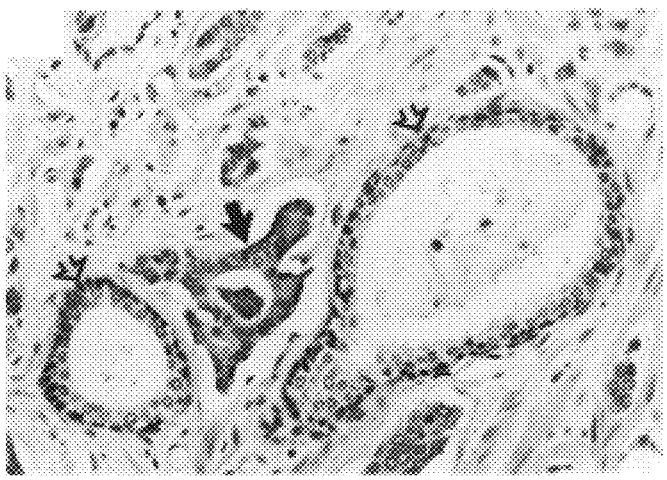
FIG. 5A, FIG. 5B, and FIG. 5C shows immunohistochemical staining of prostate tissue.
Figure 5B:
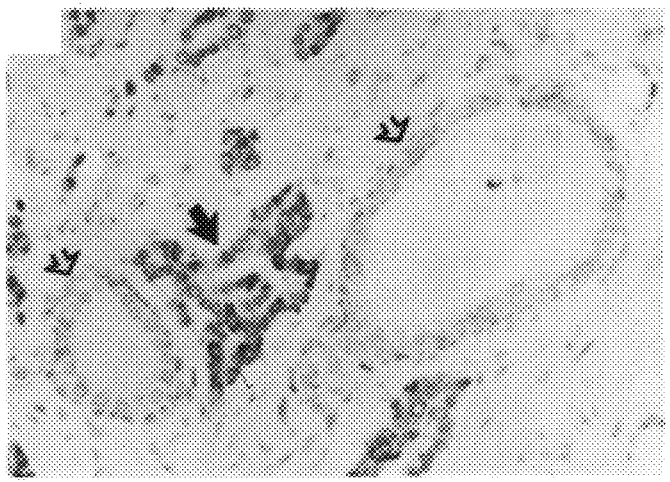
Figure 5C:
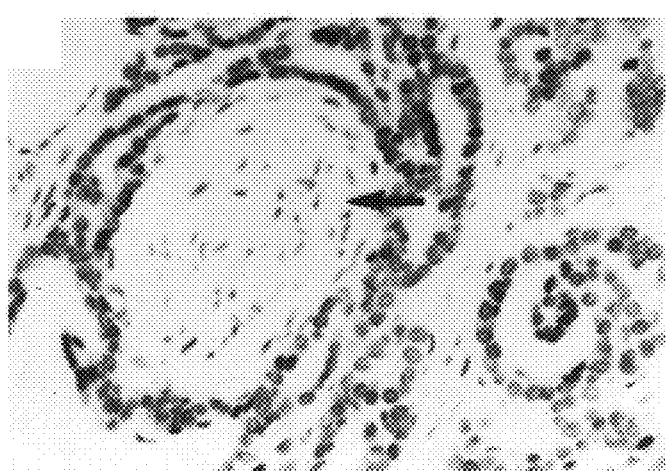

APE has also been found to be elevated in cancerous prostate tissue, and thus can similarly be used as a marker to identify cancerous states in the prostate. In particular, FIG. 5 shows immunohistochemical staining of prostate tissue, in which FIG. 5A. is hematoxylin and eosin staining of prostate tissue. FIG. 5B shows cancerous prostate cells (closed arrows) bordering normal tissue (open arrows). The level of APE is highly elevated in the prostate cancer. FIG. 5C. shows invasion of prostate nerve tissue by the cancer (filled arrows).

Figure 18A:
FIG. 18A, FIG. 18B and FIG. 18C. Prostate tissue with APE.
Figure 18B:
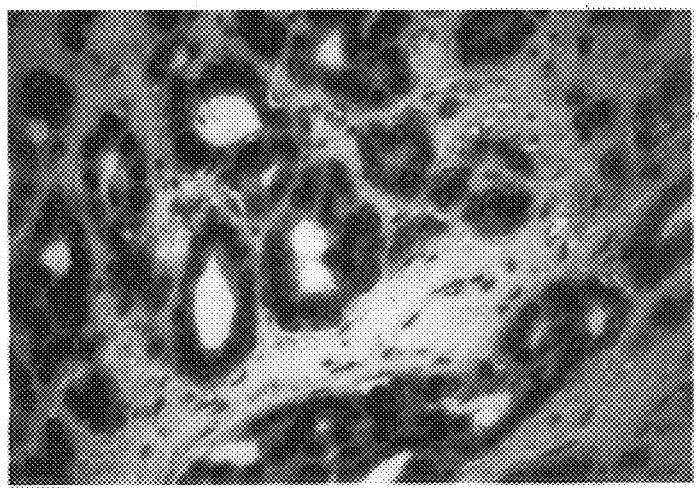
Figure 18C:

FIG. 18A, FIG. 18B and FIG. 18C also show prostate tissue with APE. FIG. 18A is a lower magnification (10×) of a section of prostate tissue showing normal (arrowheads) and cancer cells (arrows with tails). FIG. 18B is higher magnification (40%) of cancer cells from FIG. 18A showing a strong nuclear staining in a punctuate manner. FIG. 18C. low power magnification of prostate tissue with cancerous region to lower left (below arrows) and normal cells in upper right region. Distinctive higher levels of APE staining in the cancerous region can be seen.

In a further study, tissue samples were collected from the surgical pathology files of University Hospital at Indiana University School of Medicine. All tissue samples were fixed in 10% buffered formalin, embedded in paraffin and sectioned at 6 μm thickness. The prostate samples that contained malignant neoplasm were selected from cases of previously diagnosed tumors treated with prostectomy. The cases with benign lesions were obtained from transurethral resection specimens.

A semi-quantitative assessment of the specimen staining characteristic were evaluated as well as observation of the microscopic pattern. The specimens stained with antibody against APE protein were examined first without knowledge of diagnosis or microscopic features of the histologic slides. Both nuclear and cytoplasmic staining were noted. Any appreciable brown staining was considered positive and graded as 1+ if barely detectable; 2+ if easily seen fine granules were present diffusely throughout the nucleus or cytoplasm, and 3+ when dark course granules were observed. Also, the percent of cells exhibiting positive staining were estimated. Less than 10% of the cells show presence of stain were considered negative; 10%–30% of the cells positive were graded as 1+, 30%–60% as 2+ and >60% were graded as 3+. The nuclear and cytoplasmic staining were recorded separately. The H&E slides were then reviewed to determine diagnosis and map the location of the various histologic patterns such as carcinoma, glandular hyperplasia and normal to correlate with the staining patterns observed in the immunohistochemical preparations.

Figure 19A:
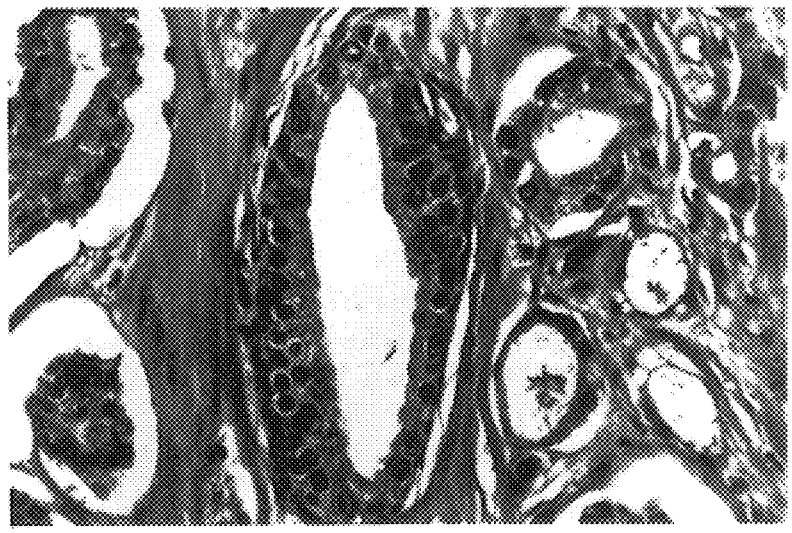
FIG. 19A, and FIG. 19B. Nuclear and cytoplasmic staining of prostate cancer cells.
Figure 19B:
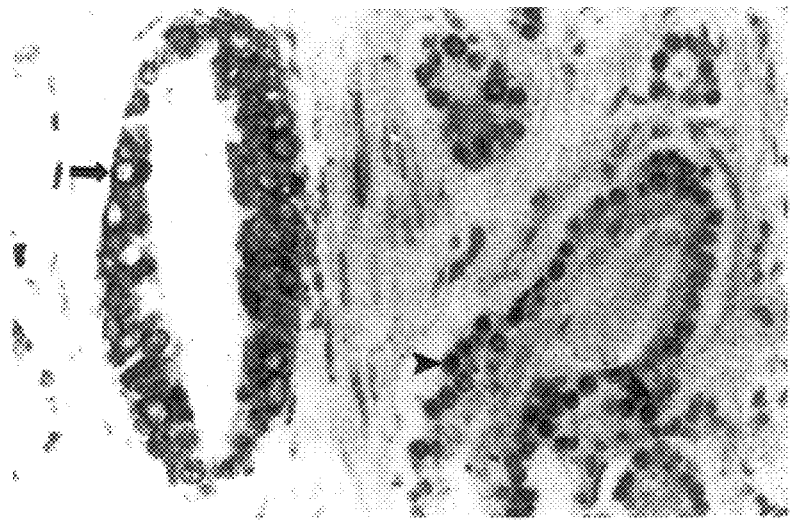

There was a distinct contrast in the staining characteristics between the areas containing malignant neoplasm and those containing benign glands (Table 5). The vast majority of the malignant tumors showed strong nuclear and cytoplasmic staining, whereas the benign areas within the slides containing adenocarcinoma as well as the glands of the cases with only benign diagnosis, showed minimal to negative staining. Five of the nine adenocarcinomas, exhibited 3+ nuclear staining in greater than 60% of the cells with similar cytoplasmic staining. One of the cases of adenocarcinoma had 2+ nuclear positivity and 2+ cytoplasmic staining. Only one exhibited 1+ nuclear staining, but it had 3+ cytoplasmic staining. Two of the malignant tumors showed negative nuclear staining, but one of these had 3+ cytoplasmic staining. The other exhibited total negative staining, raising the possibility of technical artifact. Conversely, the benign areas within the slides containing malignancy were generally negative with only rare foci showing 1+ to 2+ staining of the nuclei and cytoplasm. One of the slides consisting of glandular hyperplasia exhibited 2+ nuclear staining of 30% to 60% of the cells but expressed no cytoplasmic staining. One case of the adenocarcinoma (case 1120) showed an interesting strong punctuate supranuclear cytoplasmic staining pattern with relatively weaker nuclear staining. Also, few foci of glands with an atrophic appearance expressed strong nuclear staining. Case 835 had transitional cell carcinoma which was thought to be a good comparison with the other cases. It showed strong nuclear staining and the transitional tumor cells also extended into the prostate and was clearly visible (FIG. 19A and FIG. 19B).

TABLE 5

| No. | Case | Year | Diagnosis | Tissue | Cancer Cells | Normal cells |
|---|---|---|---|---|---|---|
| 1 | 144 | 1994 | G2 (2 + 3) | Prostate | 3+ | 0 |
| 2 | 633 | 1994 | G2 (4 + 5) | Prostate | 2+ | 0 |
| 3 | 6488 | 1995 | G2 (2 + 3) | Prostate | 3+ | 1+ |
| 4 | 6496 | 1995 | G2 (3 + 3) | Prostate | N/A | N/A |
| 5 | 315 | 1994 | G2 (3 + 4) | Prostate | 3+ | 0 |
| 6 | 597 | 1995 | hyperplasia | Prostate | N/A | N/A |
| 7 | 1120 | 1995 | G3 | Prostate | 2+ | 0 |
| 8 | 835 | 1995 | TCC/Nod. Hyperplasia | Prostate | 3+ | |
| 9 | 1157 | 1995 | G2 | Prostate | 3+ | 0 |
| 10 | 1931 | 1995 | G2 | Prostate | 3+ | 0 |
| 11 | 1687 | 1995 | G2 | Prostate | 2+ | 0 |
| 12 | 835 | 1995 | TCC | Prostate | 3+ | 0 |

Example 5

APE Expression in Differentiating Myeloid Leukemia Cells

To investigate possible changes in expression of the DNA repair enzyme APE in differentiating myeloid cells, the inventor utilized Northern and Western blot analysis with the HL-60 myeloid leukemia cell line, which can be induced to terminally differentiate into mature granulocytes or monocyte/macrophage (Collins, 1987). Western blot analysis revealed a progressive decrease in APE protein expression over 6 days in HL-60 cells induced to differentiate along the granulocytic pathway with $10^{-5}$ M RA compared to ethanol treated controls (FIG. 6A). A more rapid decrease in APE expression was observed with granulocytic induction using DMSO (FIG. 6A) with nearly undetectable APE after 6 days. These observations were confirmed by Northern blot analysis (FIG. 6A) where a similar progressive decrease in APE transcript expression was observed with induction of granulocytic differentiation. Again DMSO induces a more rapid decrease to a lower level compared to RA. To determine whether the decrease in APE expression was confined to granulocytic differentiation, HL-60 cells were induced down the monocyte/macrophage pathway with PMA. Expression of the APE protein decreased to a very low level by Western blot (FIG. 6B) after two days exposure to PMA. Decreased expression of the APE transcript on Northern blot was also evident after exposure to PMA (FIG. 6B). Thus, induction of granulocytic and monocytic differentiation in HL-60 cells results in decreased expression of APE at the RNA and protein level.

Example 6

Figure 10A:
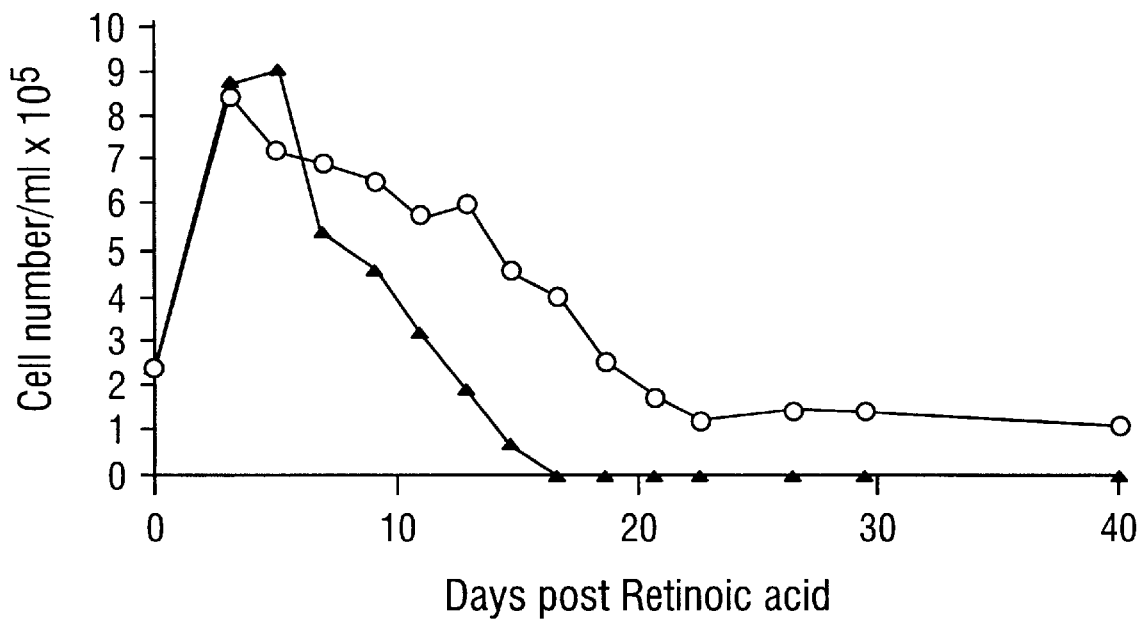
FIG. 10A and FIG. 10B: Enhanced viability of HL-60-bcl-2 granulocytes. HL-60 and HL-60-bcl-2 cells were induced with RA (1 μmol/L) which was added at day 0. At the indicated days after RA treatment (FIG. 10A), cell number was determined using a hemocytometer chamber and (FIG. 10B) percentage of cell viability was determined by trypan blue dye exclusion. The indicated points represent the mean of triplicate experiments (▲) HL-60 wt; (○) HL-60 Bcl2.
Figure 10B:
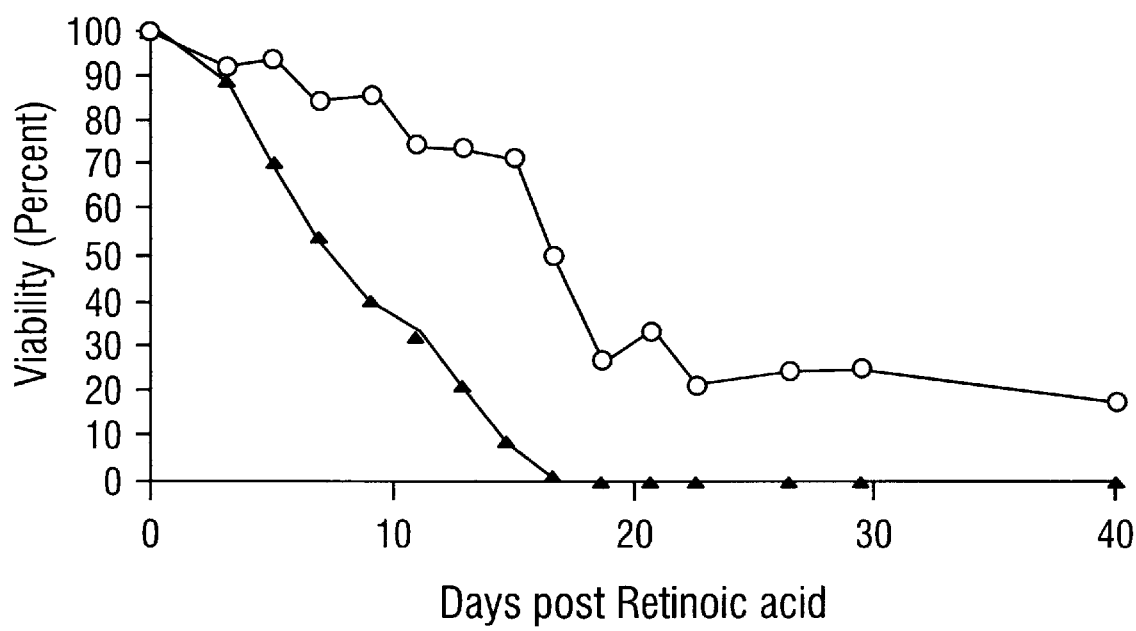
Figure 11A:
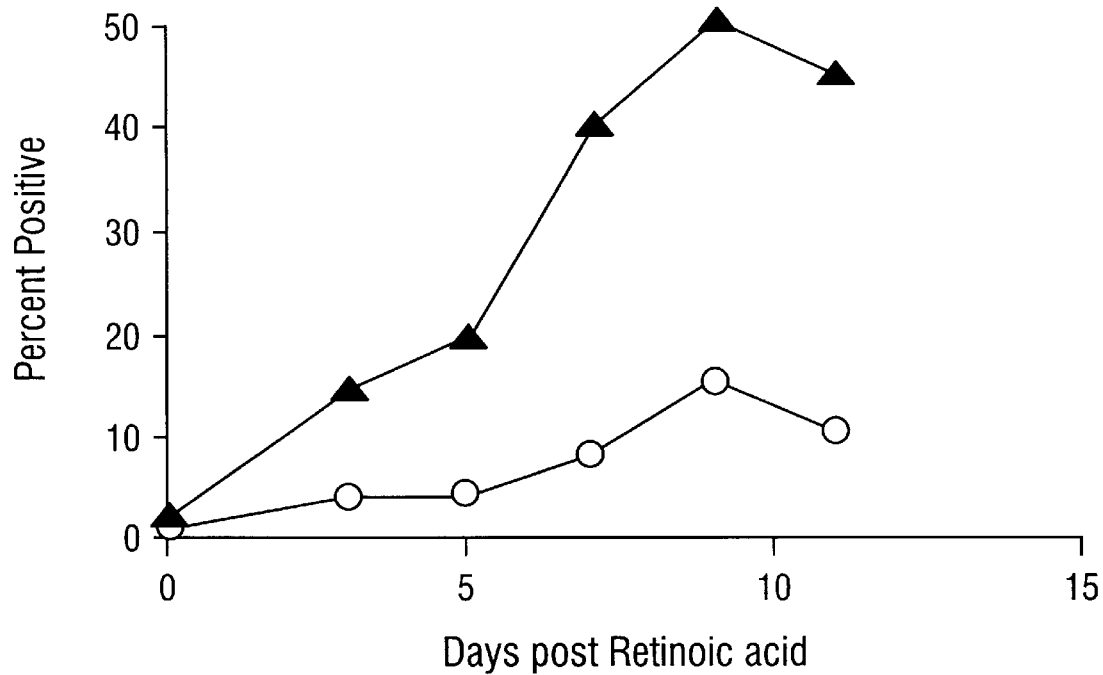
FIG. 11A and FIG. 11B: Reduced DNA fragmentation in induced HL-60-bcl-2 granulocytes. HL-60 and HL-60-bcl-2 cells were induced with RA (1 μmol/L) which was added at day 0.
Figure 11B:
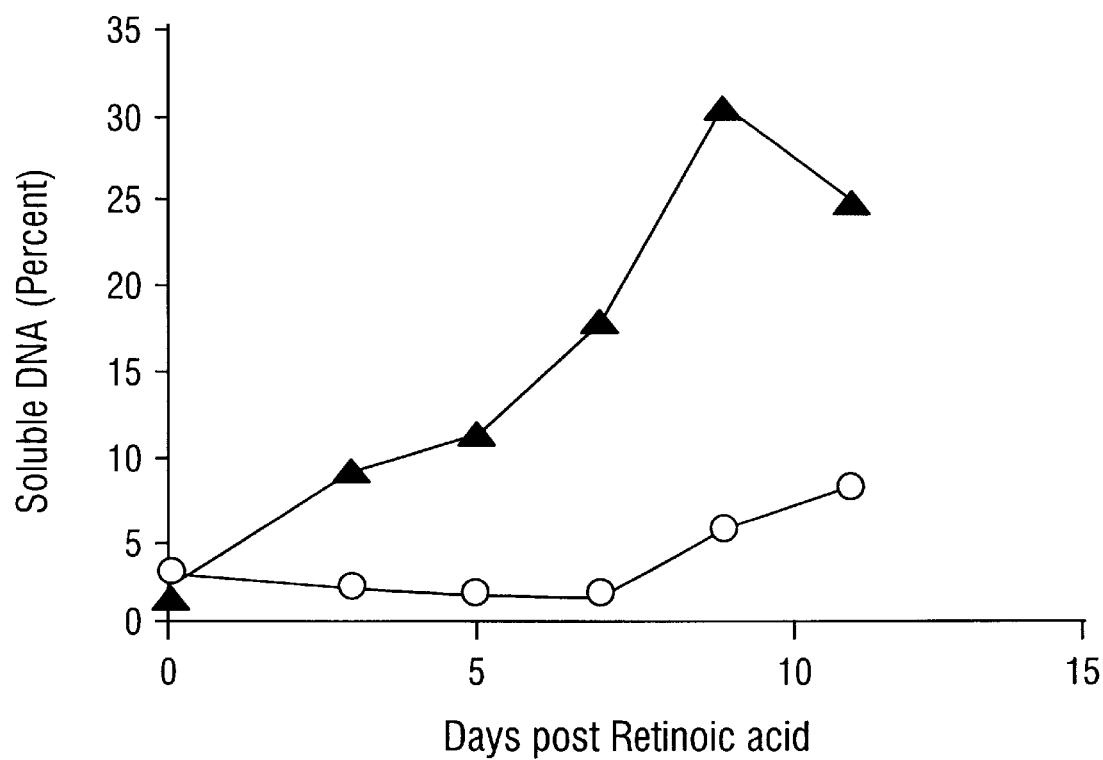

Overexpression of the bcl-2 oncogene in HL-60 cells inhibits apoptosis does not affect retinoic acid induced differentiation To determine whether cell differentiation and apoptosis were closely linked processes that could not be separated, the inventor over expressed the proto-oncogene bcl-2 in HL-60 cells to block apoptosis. the 1.9 kB cDNA of bcl-2 was subdloned into the retroviral vector LXSN to produce Lbcl2SN. The ecotropic packaging cell line PE501 was transfected and used to transduce the amphotropic packaging cell line PA317. High titer clones of PA317+Lbcl2SN were selected for transduction of HL-60 cells to produce HL-60+Lbcl2SN. Several clones were screened by Northern blot analysis and one clone with high bcl-2 expression was chosen for study. Treatment of the HL-60 +Lbcl2SN cells with RA resulted in well differentiated mature granulocytes (metamyelocytes, myelocytes, bands and neutrophils) expressing CD11b (Table 6). These cells were assayed for programmed cell death using the TUNNEL reaction to score individual cells and the diphenylamine assay to determine the total amount of DNA undergoing fragmentation. The transduced HL-60+Lbcl2SN cells treated with RA had a much lower level of apoptosis (FIG. 10A and FIG. 10B) and enhanced viability with survival of mature granulocytes up to 40 days compared to the parental HL-60 cells treated with RA (FIG. 11A and FIG. 11B). Thus myeloid cell differentiation and apoptosis are independent processes that can be separated.

TABLE 6

RA-Induced Differentiation of HL-60 and HL-60-bcl-2 Cells

|  | HL-60 | | HL-60-bcl-2 | |
| --- | --- | --- | --- | --- |
|  | (−) RA | (+) RA | (−) RA | (+) RA |
| Mature myeloid cells (%)[1] | <5 | 86 = 6 | 7 = 3 | 88 = 5 |
| CD11b (+)[2] | 69.2 | 105.4 | 59.1 | 107.9 |
| NBT (+)[3] | <5 | >90 | 5 | >90 |

Cells were induced with RA (1 mmol/L) for 7 days and evaluated by morphology. CD11b surface antigen expression. and NBT reduction.
[1]Myelocytes, metamyelocytes, banded and segmented granulocytes on Wright-Giemsa-stained preparations of cell suspensions. Numbers represent the average percentage: The observed range in triplicate experiments.
[2]Results are expressed as the relative mean fluorescence on an arbitrary log scale from 0 to 200 where an increment of 18.5 U represents a doubling of fluorescent intensity. Data on 5,000 cells were analyzed for each sample.
[3]Percentage of cells containing blue-black formazan deposits after 1 hour of TPA stimulation.

Example 7

APE Expression and bcl-2 Expression

Figure 7B:
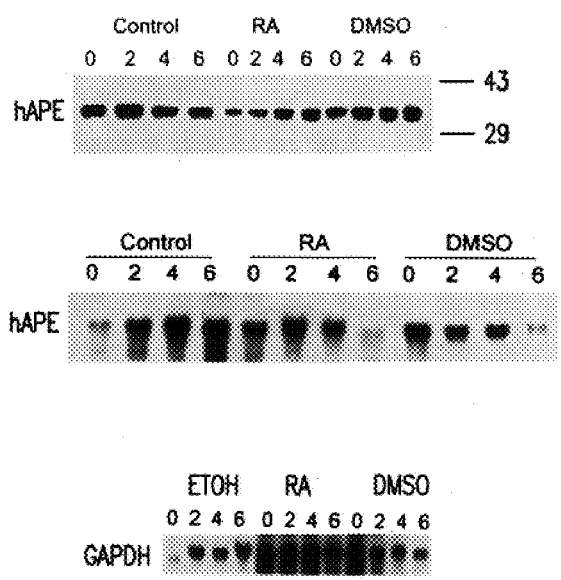
FIG. 7A and FIG. 7B: Expression of APE in HL-60-bcl-2 cells.
Figure 7A:
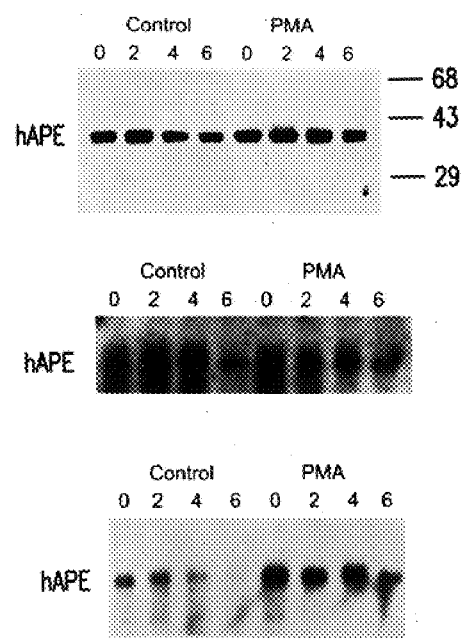
Figure 8A:
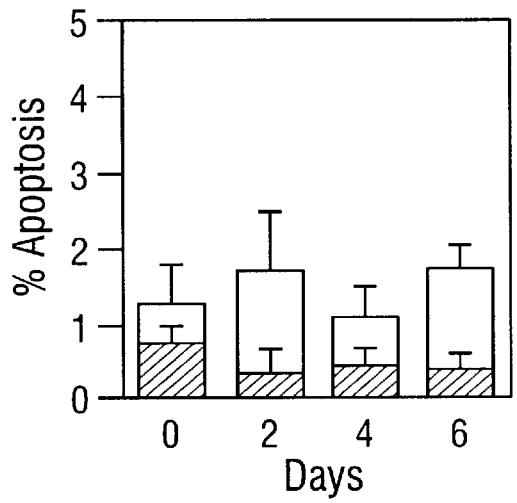
FIG. 8A, FIG. 8B, FIG. 8C and FIG. 8D: Apoptosis in HL-60 (open boxes) and HL-60-bcl-2 (black boxes) cells after differentiation induction. Percent apoptotic cells was determined by counting cells staining positive for the TUNNEL reaction. Cells were treated with ethanol (control.
Figure 8B:
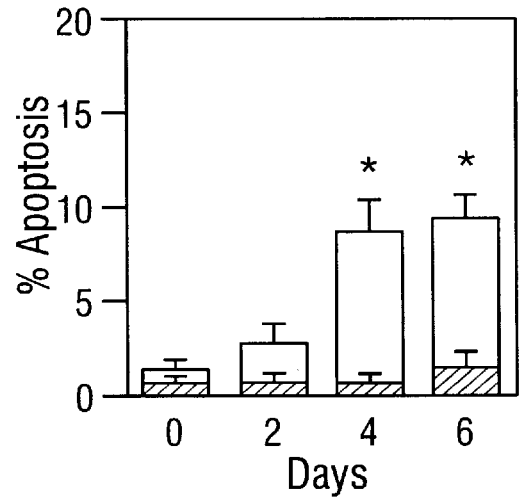
Figure 8C:
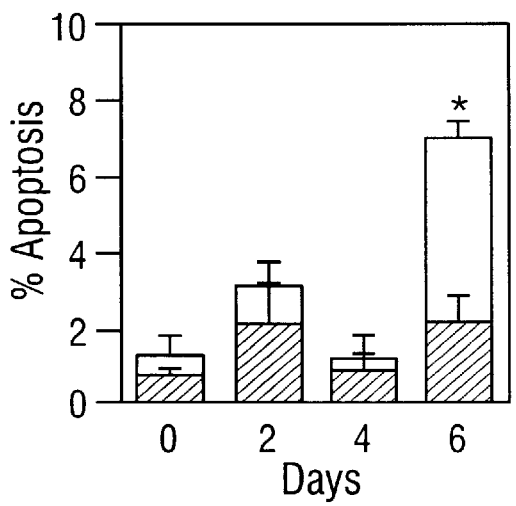
Figure 8D:
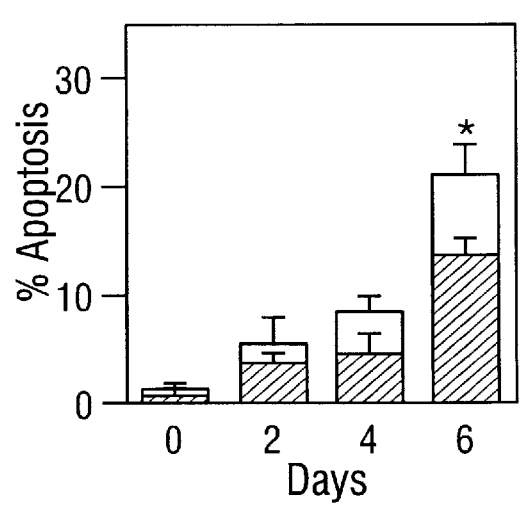

To ascertain whether APE expression was associated with differentiation or programmed cell death, the inventor blocked apoptosis by over-expression of the proto-oncogene bcl-2 using HL-60 cells transduced with the retroviral construct Lbcl2SN (Park et al., 1994). Western blot analysis of the HL-60-bcl-2 cells induced down the granulocytic pathway with RA or DMSO revealed continuous expression of APE compared to the rapid decrease in expression observed with similar treatment of the parental HL-60 cells (FIG. 6A and FIG. 7A). Expression of APE mRNA in the HL-60-bcl-2 cells after exposure to RA or DMSO is similarly maintained paralleling the protein expression (FIG. 7A). The apparent decrease in APE transcript expression after 6 days exposure to RA or DMSO results from loading differences as evidenced by the GAPDH Northern control blot (FIG. 7). Monocyte/macrophage differentiation induction of HL-60-bcl-2 cells with PMA also revealed continuous expression of APE both at the protein and RNA level (FIG. 7B). Thus constitutive expression of bcl-2 inhibits the decrease in APE expression as well as programmed cell death normally observed with granulocytic or monocytic/macrophage induced differentiation of HL-60 cells.

Example 8

APE Expression And Programmed Cell Death

The correlation between the decreased expression of APE in induced HL-60 cells and programmed cell death was examined by quantitating the number of cells undergoing apoptosis in induced HL-60 and HL-60-bcl-2 cells using the in situ TUNNEL assay. There is a baseline low incidence (1–2%) of apoptosis in HL-60 cells that does not change following ethanol (FIG. 8) and probably reflects the few HL-60 cells that can be observed to spontaneously differentiate in untreated growing cultures. Over-expression of bcl-2 depresses the baseline apoptosis to less than 1% (FIG. 8). Granulocytic differentiation induction (RA, DMSO), as well as monocyte/macrophage differentiation induction (PMA) resulted in a statistically significant inhibition of apoptosis by day 6 in the HL-60-bcl-2 cells compared to the wild type HL-60 cells (FIG. 8). The high level expression of bcl-2 in HL-60-bcl-2 cells appears to be responsible for not only the block in apoptosis (Park et al., 1994), but also the failure to downregulate expression of APE with induction of differentiation. Hence, the bcl-2 transduced HL-60 cells differentiate (RA, DMSO, or PMA) morphologically but do not undergo apoptosis and do not exhibit decreased expression in APE, thus establishing the inverse relationship between programmed cell death and APE expression. This leads to the conclusion that the decrease in expression of APE observed on Northern and Western blot (FIG. 6) in induced HL-60 cells is associated with programmed cell death.

Figure 9A:
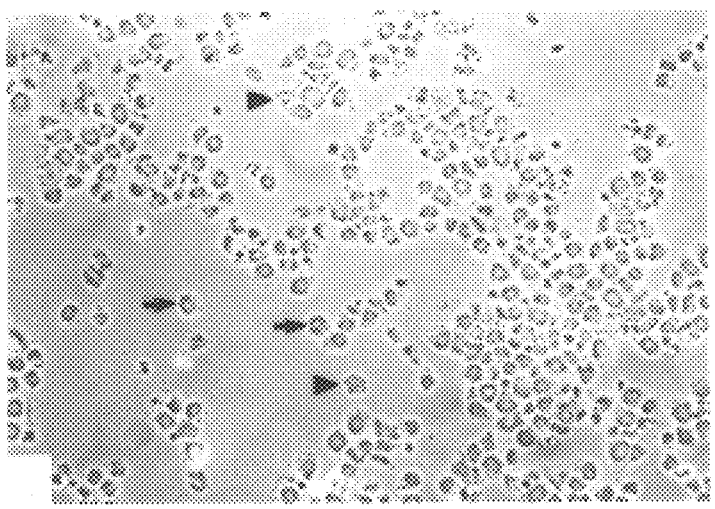
FIG. 9A, FIG. 9B and FIG. 9C: Specificity of APE expression down-regulation and apoptosis.
Figure 9B:
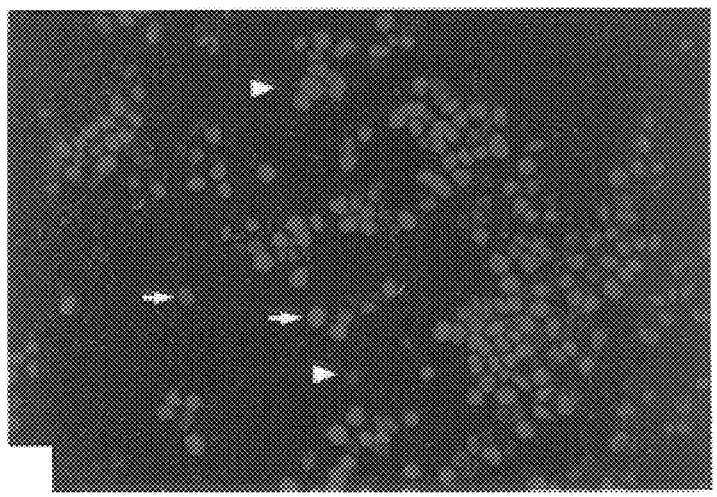
Figure 9C:
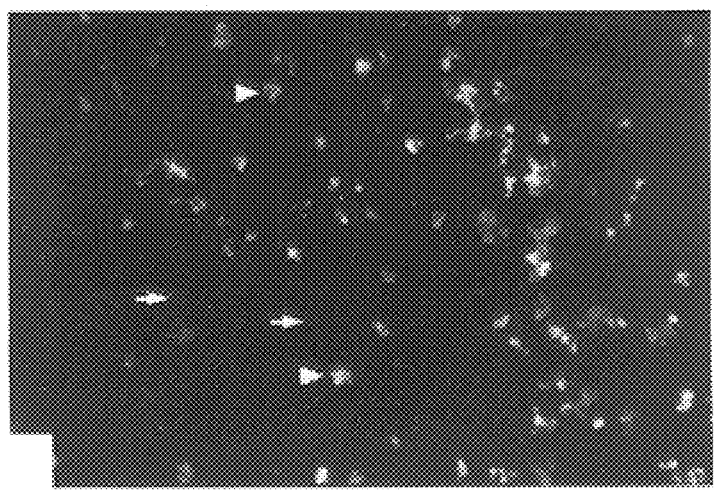

To determine if the cells undergoing apoptosis were also the cells downregulating APE, double labeling experiments were performed on a 50:50 mix of untreated and RA treated (6 days, $10^{-5}$ M) HL-60 cells (FIG. 9A). Cytocentrifuge preparations were stained for 1) fragmented DNA using fluorescein-dUTP in the TUNEL assay (FIG. 9C) and 2) APE using polyclonal rabbit anti-APE with a rhodamine labeled goat anti-rabbit secondary antibody (FIG. 9B). Cells undergoing apoptosis fluoresce 'green' and cells expressing APE fluoresce 'red'. Examination of the cells revealed that cells staining positive with the TUNEL assay, thus undergoing apoptosis, had little or no APE as evidenced by the absence of rhodamine fluorescence. Conversely, TUNEL negative cells, not undergoing apoptosis, stained strongly positive for APE. Thus, HL-60 cells undergoing apoptosis appear to lose expression of APE.

The inventor further characterized the temporal decline in APE expression to see if it was an early event in programmed cell death or if the decline coincided with fragmentation of DNA (TUNEL assay); the inventor assayed APE expression and DNA fragmentation on cytospun preparations of cells after exposure to DMSO. The expression of APE started to fall with fewer rhodamine positive cells after 2 days of DMSO while statistically significant evidence of fragmented DNA was not apparent until after 4–6 days (Table 7, FIG. 8). A similar pattern was observed, but not as rapid a loss of APE expression, after exposure to RA or PMA. Thus the decrease in APE expression associated with programmed cell death appears to be an early event occurring before the final pathologic consequences of DNA fragmentation in apoptosis.

TABLE 7

Temporal relationship of AP endonuclease expression to apoptosis

| Cells | % rhodamine positive (APE) | % fluorescein positive (TUNEL) |
| --- | --- | --- |
| HL-60 control | 77% | 1.7% |
| HL-60 + DMSO 2 days | 34% | 2.7% |
| HL-60 + DMSO 4 days | 0% | 2.3% |
| HL-60 + DMSO 6 days | ND | 7% |

Therefore, the present study, associates apoptosis with downregulation of APE. The identification of a functional relationship and which APE domains might be involved in programmed cell death awaits further experiments will be elucidated with retroviral transduction of various APE constructs into cells as described in Example 6 and above.

Example 9

Figure 12A:
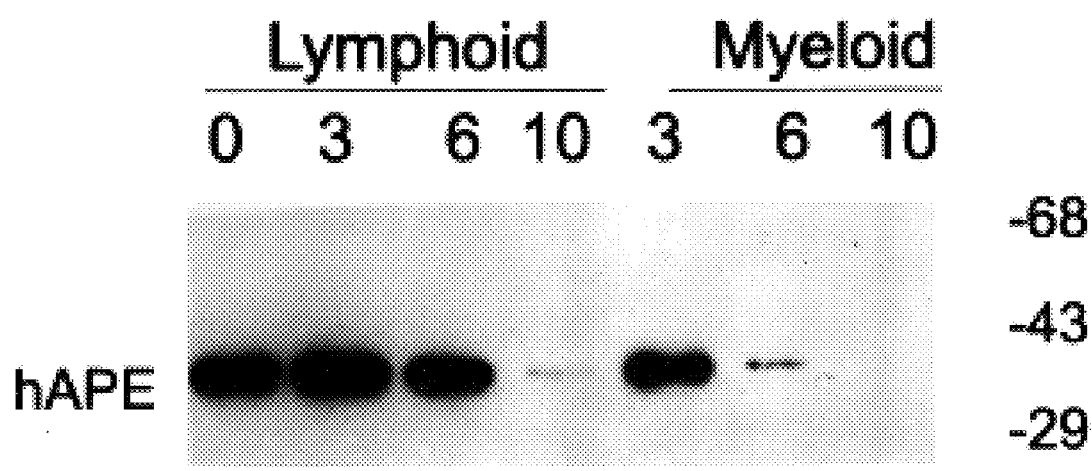
FIG. 12A and FIG. 12B. Northern and Western blot analyses of APE expression in CD34 cells induced to differentiate down the lymphoid and myeloid pathways
Figure 12B:
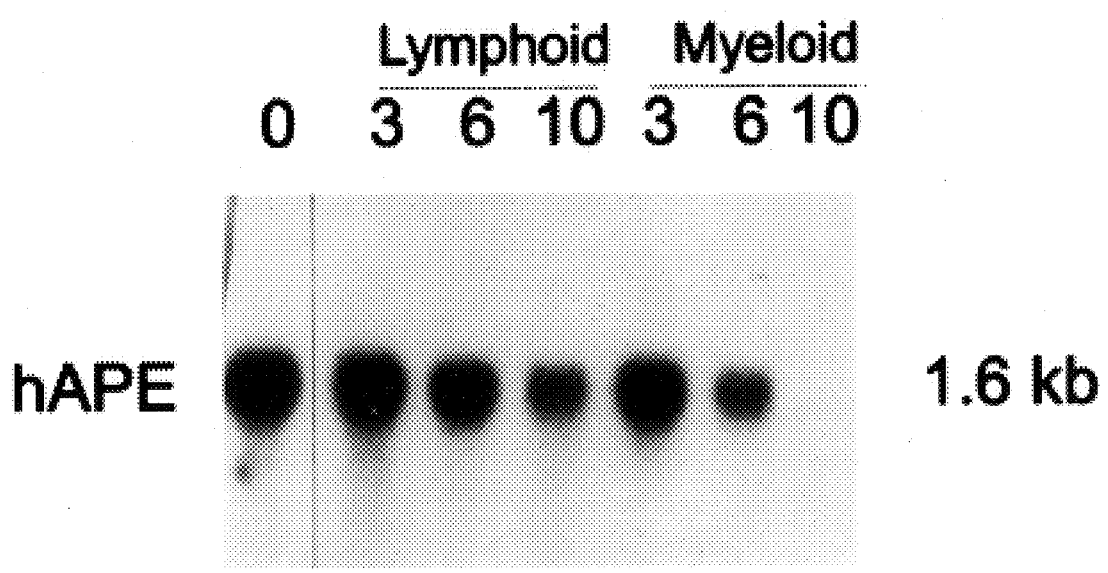

APE as a Marker of Apoptosis in Human cells Differentiating CD34± peripheral blood stem cells downregulate APE The expression of APE in peripheral blood stem cells was examined to see if APE expression would mimic what was observed with HL-60 cells. Peripheral blood mononuclear cells were obtained after informed consent by apheresis of volunteer adult subjects following 5 days of G-CSF mobilization. CD34+ cells were isolated using a MACS column. Highly pure (88+/−6% mean +/−SD, n=7) CD34+ cells were obtained with high recovery (77+/−7%, n=7). CD34+ cells were subsequently grown in the presence of human stem cell factor (SCF) and interleukin (IL)-7 for lymphoid differentiation or SCF, IL-6 and G-CSF for myeloid differentiation. Adequate numbers of cells were collected at days 0, 3, 6 and 10 to allow analysis both by Northern blots of RNA (probed with the human APE cDNA) and Western blots of protein using affinity purified antibody to human APE. FLOW analysis and morphologic examination confirmed the differentiated phenotype of the cells after culture. APE mRNA and protein demonstrated a dramatic decrease during myeloid differentiation with easily detectable levels present at day 0 falling to undetectable levels after 10 days of differentiation. mRNA and protein levels correlated (FIG. 12A and FIG. 12B). A less dramatic fall in expression of APE was seen in lymphoid culture conditions. Apoptosis, measured by FLOW and confirmed by TUNEL assay staining of cytospin preparations, increased during differentiation. The level of apoptosis inversely correlated with expression of APE, ie., was significantly higher in myeloid cells. These data support the hypothesis that down-regulation of APE is an early event in cells undergoing apoptosis and reduced expression of APE may explain the increased sensitivity of more differentiated myeloid cell populations versus hematopoietic stem cells to alkylating agent cytotoxicity.

Example 10

Retroviral APE Constructs

As discussed above, recombinant retrovirus vectors are a highly efficient method to introduce exogenous genes into hematopoietic cells as well as cell lines. Myeloid cell lines, such as used by the inventor are often difficult to transfect with standard expression plasmids using normal molecular biology techniques. For that reason, as well as the potential clinical use of the APE gene for gene transfer studies into primary hematopoietic cells, the inventor have developed recombinant retrovirus vectors to infect and express the recombinant APE gene and the various permutations of the APE gene.

Figure 13:
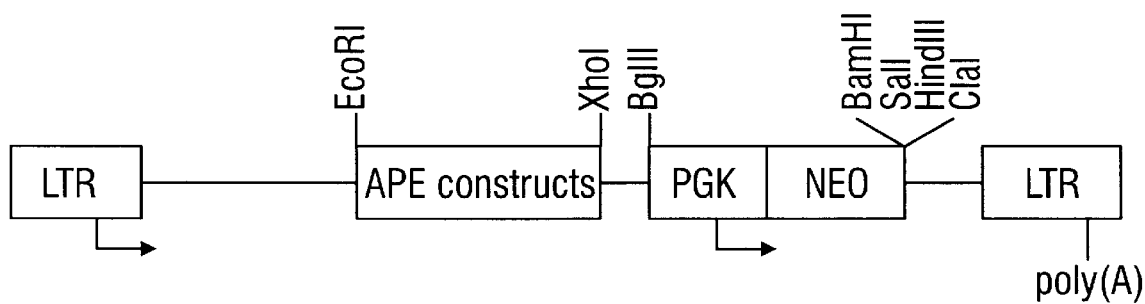
FIG. 13: Schematic representation of retroviral constructs containing the human APE cDNA.
Figure 14:
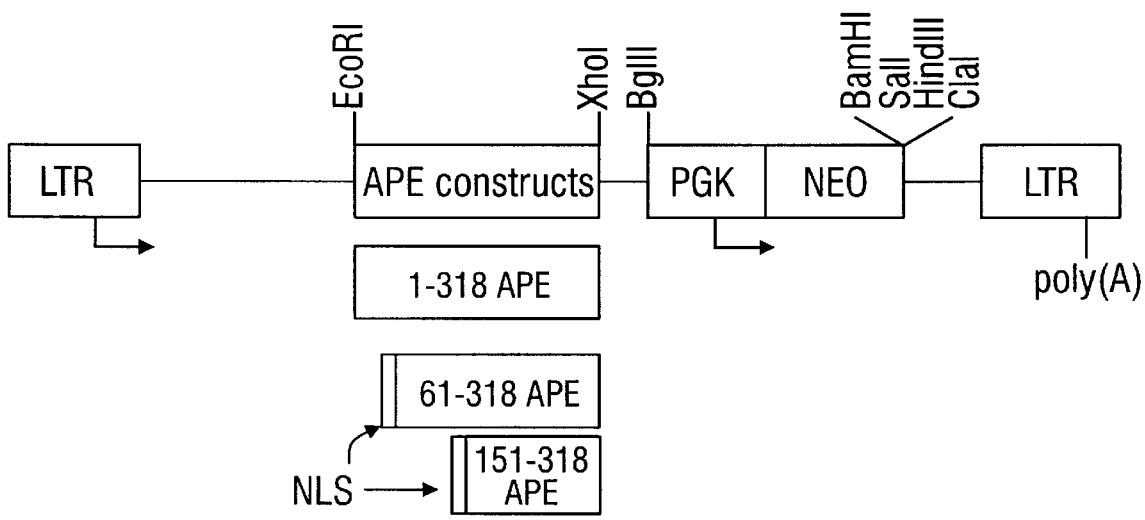
FIG. 14: Additional APE constructs.

The retrovirus backbone that chosen is based on the Murine Stem Cell Virus backbone that has been previously described (Hawley et al., 1993). The encoded genes are expressed from a myeloproliferative sarcoma virus LTR. The vector includes long gag sequences to promote higher titer virus production in retrovirus packaging cells, but contains mutations which interfere with gag-related protein synthesis and expression of env-related proteins. The constructs containing the human APE cDNAs are completed and an example is schematically shown in FIG. 13 and FIG. 14.

The retroviral plasmid is transfected into the packaging lines GP+E86 and GP+AM12 (Markowitz et al., 1988a; Markowitz et al., 1988b). The helper virus genome of the packaging line is separated onto two plasmids. The packaging signal and 3' LTR have been removed. Construction of these retroviral lines make the generation of recombinant retrovirus unlikely since at least three recombinational events must occur prior to generation of wild type virus. The GP+E86 producer line contains a env gene which encodes for a viral envelope protein allowing for the infection of a narrow group of animals, specifically rodents such as mouse and rat (ecotropic range). The GP+AM12 has an envelope protein that allows for the infection of a broad range of animals including rodents and primates.

Individual packaging cell clones are isolated by selecting transfected cells in 1 mg G418 powder/ml (GIBCO/BRL, Gaithersburg, Md.). Individual G418 resistant clones are expanded and assayed for retrovirus production as previously described (Clapp et al., 1995). Briefly, serial dilutions of retrovirus supernatant from individual clones were assayed for the ability to transmit G418 resistance (1 mg/ml) to NIH3T3 cells. Supernatant is collected following clonal expansion of producer cells to confluence on plates and the addition of 8 ml of fresh media for 14–16 hours collection. Supernatant is filtered through a 0.45 mm filter and limiting dilutions of viral supernatant were added to 100 mm$^2$ plates of NIH3T3 cells grown to approximately 30–40% confluence and cultured with 6 μg/ml of polybrene for 2 hours followed by the addition of 8 ml of media. The cells were then allowed to grow to confluence, split onto three 100 mm$^2$ plates and selected in 1 mg/ml of G418.

In order to determine if the APE gene product can regulate or alter the endogenous APE gene in HL60 cells, the various APE constructs are used to transduce HL60 cells. Cells are infected using virus supernatant infections as previously described (Clapp et al., 1995) and then selected in 1 mg/ml of G418 to remove all untransduced cells. Clones are picked for insertion (Southern blot) and expression levels (Northerns and Westerns) of the APE gene). Various clones can be picked with high, intermediate and low levels of retroviral APE production.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are indicative of the level of skill in the art and are hereby incorporated herein by reference as if each had been individually incorporated by reference where cited above and fully set forth.

The following references are indicative of the level of skill in the art and are hereby incorporated herein by reference as if each had been individually incorporated by reference where cited above and fully set forth.

Agarwal S., S. Sharma, "Localization Of Carcinoembryonic Antigen In Uterine Cervical Neoplasia," *Indian J Med. Res.*, Vol. 92, pp 452–455 (1990).

Auger M., T. J. Colgan, "Of Metastatic Vulvar And Cervical Squamous Carcinoma In Regional Lymph Nodes By Use Of A Polyclonal KeratinAntibody," *Int. J Gynecol. Pathol.*, Vol. 9, pp 337–342 (1990).

Baichwal and Sugden, "Vectors for gene transfer derived from animal DNA viruses: Transient and stable expression of transferred genes", In: *Gene Transfer*, Kucherlapati R., ed., New York, Plenum Press, 117–148, 1986

Bamford P. M., et al., "An Immunohistochemical Study Of The Distribution Of Epithelial Antigens In The Uterine Cervix," *Obstet. Gynecol.*, Vol. 61, pp 603–608 (1983).

Bamford P. N., et al., "An Immunohistochemical Study Of The Distribution Of Epithelial Antigens In The Uterine Cervix," *Obstet. Gynecol.*, Vol. 61, pp 603–608 (1983).

Barany and Merrifield, "The Peptides, Gross and Meienhofer, eds", *Academic Press, New York*, 1–284, 1979

Barzilay G and Hickson ID "Structure and function of apurinic/apyrimidinic endonucleases." *Bioessays*, 17 (8) p713–9, 1995

Barzilay G et al, "Identification of critical active-site residues in the multifunctional human DNA repair enzyme HAP1." *Nat Struct Biol.*, 2 (7) p561–8, 1995

Barzilay G; et al., "Site-directed mutagenesis of the human DNA repair enzyme HAP1:identification of residues important for AP endonuclease and RNase H activity." *Nucleic Acids Res.*, 23 (9) p1544–50, 1995

Bellus,*J Macromol. Sci. Pure,AppL. Chem*, A31(1): 1355–1376, 1994

Benvenisty & Neshif, "Direction introduction of genes into rats and expression of the genes," *Proc. Nat. Acad. Sci. USA*, 83:9551–9555, 1986

Burger, et al., "Antibodies to human plasma kallikrein from egg yolks of an immunized hen: preparation and characterization," *Thrombosis Res.*, 40:283–288, 1985

Bychkov V., et al., "Immunocytochernical Localization Of Carcinoembryonic Antigen (CEA), Alpha-Fetoprotein (AFP), And Human Chorionic Gonadotropin (HCG) In Cervical Neoplasia, " *Am. J Clin. Pathol.*, Vol. 79, pp 414–420 (1983).

Campbell, In: *Monoclonal Antibody Technology. Laboratory Techniques in Biochemistry and Molecular Biology*, Vol. 13, Burden & Von Knippenberg (Eds.), Elseview, Amsterdam, pp. 75–83, 1984.

Capaldi et al., *Biochem. Biophys. Res. Comm.*, 76:425, 1977

Cardillo M. R., et al., "*Immunohistochemical Analysis* Of p53 Oncoprotein And Proliferating Cell Nuclear Antigen In The Cervix Uteri," *Eu. J Gynaec. Oncol.*, Vol. 14, pp 484–490 (1993).

Carico, E. et al., "Integrin Beta 4 Expression In The Neoplastic Progression Of Cervical Epithelium," *Gynecol. Oncol.*, Vol. 49, pp 61–66 (1993).

Cech T R et al., "In vitro splicing of the ribosomal RNA precursor of Tetrahymena: involvement of a guanosine nucleotide in the excision of the intervening sequence. Cell, 27 (3 Pt 2) p487–96, 1981.

Chang et al., "Foreign gene delivery and expression in hepatocytes using a hepatitis B virus vector" *Hepatology*, 14:124A, 1991

Chen and Okayama, "High-efficiency transfection of mammalian cells by plasmid DNA," *Mol. Cell Biol.*, 7:2745–2752, 1987

Clapp D W et al., "Myeloproliferative sarcoma virus directed expression ofbetagalactosidase following retroviral transduction of murine hematopoietic cells." *Exp. Hematol.* 23 (7) p630–8,. Jul 1995

Codegoni, et al., "Expression of Genes of Potential Importance in the Response to Chemotherapy and DNA Repair in Patients with Ovarian Cancer", *Gynecologic Oncology* 65:130–137, 1997

Coffin, "Retroviridae and their replication," In: Fields BN, Knipe DM, ed. Virology. New York: Raven Press, 1437–1500, 1990

Collins S J "The HL-60 promyelocytic leukemia cell line: proliferation, differentiation, and cellular oncogene expression." *Blood*, 70 (5) p1233–44, 1987

Costa S., et al., "Monoclonal Antibody To HSV2 Protein As An Immunodiagnostic Marker In Cervical Cancer," *Cancer Detect. Prev. Suppl.*, Vol. 1, pp 189–205 (1987).

Couch et al., "Immunization with types 4 and 7 adenovirus by selective infection of the intestinal tract," *Am. Rev. Resp. Dis.*, 88:394–403, 1963

Coupar et al., "A general method for the construction of recombinant vaccinia virus expressing multiple foreign genes", *Gene*, 68:1–10, 1988

Crombach G., et al., "Detection Of Squamous Cell Carcinoma Antigen In Normal Squamous Epithelia And In Squamous Cell Carcinomas Of The Uterine Cervix," *Cancer*, Vol. 63, pp 1337–1342 (1989).

Davis, F. G. et al., "Cancer Incidence Of Hispanics And Non-Hispanic Whites In Cook County, Illinois," *Cancer*, Vol. 75, pp 2939–2945 (1995).

Demple, et al., "Cloning And Expression Of APE, The cDNA Encoding The Major Human Apurinic Endonuclease: Definition Of A Family Of DNA Repair Enzymes", *Proc. Natl. Acad. Sci. U.S.A.*, 88:11450–11454, 1991

Demple, et al., "Cloning And Expression Of APE, The cDNA Encoding The Major Human Apurinic Endonuclease: Definition Of A Family Of DNA Repair Enzymes", *Proc. Natl. Acad. Sci. U.S.A.*, 88:11450–11454,1991

Dubensky et al, "Direct transfection of viral and plasmid DNA into the liver or spleen of mice," *Proc. Nat. Acad. Sci. U.S.A.*, 81:7529–7533, 1984

Duguid, et al., "Differential Cellular And Subcellular Expression Of The Human Multifunctional Apurinic/ Apyrimidinic Endonuclease (APE/ Ref-1) DNA Repair Enzyme", *Cancer Res.*, 55:6097–6102, 1995

Eliot, et al., "Differential oncoene expression and susceptibility to apoptosis in the human leukemia HL60 cell lines: Implications for etoposide resistance", *Anticancer Res.*, 15:729–734, 1995

Fechheimer et al., "Transfection of mammalian cells with plasmid DNA by scrape loading and sonication loading," *Proc. Natl. Acad. Sci. U.S.A.*, 84:8463–8467, 1987

Ferkol et al., "Regulation of the phosphoenolpyruvate carboxykinase/human factor IX gene introduced into the livers of adult rats by receptor-mediated gene transfer", *FASEB J.*, 7:1081–1091, 1993

Flint, A. et al., "Cervical Carcinoma Antigen: Distribution In Neoplastic Lesions Of The Uterine Cervix And Comparison To Other Tumor Markers," *Gynecol. Oncol.*, Vol. 30, pp 63–70 (1988).

Fodor et al., "Light-directed, spatially addressable parallel chemical synthesis", *Science*, 251:767–773, 1991

Forster & Symons, "Self-cleavage of plus and minus RNAs of a virusoid and a structural model for the active sites," *Cell*, 49:211–220, 1987

Fraley et al, "Entrapment of a bacterial plasmid in phospholipid vesicles: Potential for gene transfer," *Proc. Natl. Acad. Sci. U.S.A.*, 76:3348–3352, 1979

Fraley et al, "Entrapment of a bacterial plasmid in phospholipid vesicles: Potential for gene transfer," *Proc. Natl. Acad. Sci. U.S.A.*, 76:3348–3352, 1979

Freshner, "Animal Cell Culture: a Practical Approach", Second Edition, Oxford/New York, IRL Press, Oxford University Press, 1992

Freshner, "Animal Cell Culture: a Practical Approach", Second Edition, Oxford/New York, IRL Press, Oxford University Press, 1992

Friedmann, "Progress toward human gene therapy," *Science*, 244:1275–1281, 1989

Frohman, In: *PCR Protocols: A Guide To Methods And Applications*, Academic Press, N.Y., 1990

Fuchs P. G., et al., "Human Papillomavirus 16 DNA In Cervical Cancers And In Lymph Nodes Of Cervical Cancer Patients: A Diagnostic Marker For Early Metastases?," *Int. J. Cancer*, Vol. 43, pp 41–44 (1989).

Gefter et al., *Somatic Cell Genet.*, 3: 231–236, 1977

Gerlach et al., "Construction of a plant disease resistance gene from the satellite RNA of tobacco rinspot virus," *Nature (London)*, 328:802–805, 1987

Ghosh-Choudhury et al, *EMBO J*, 6:1733–1739, 1987

Ghosh and Bachhawat, "Targeting of liposomes to hepatocytes," In: Wu G, Wu C ed. Liver diseases, targeted diagnosis and therapy using specific receptors and ligands. New York: Marcel Dekker, 87–104, 1991

Gingeras et al., PCT Application WO 88/10315.

Goding, In: *Monoclonal Antibodies: Principles and Practice*, 2d ed. Academic Press, Orlando, Fla., pp. 60–61, 65–66, 71–74, 1986.

Gomez-Foix et al., "Adenovirus-mediated transfer of the muscle glycogen phosphorylase gene into hepatocytes confers altered regulation of glycogen," *J. Biol. Chem.*, 267:25129–25134, 1992

Gopal, "Gene transfer method for transient gene expression, stable transfection, and cotransfection of suspension cell cultures," *Mol Cell Biol.*, 5:1188–1190, 1985

Graham & Van Der Eb, "A new technique for the assay of infectivity of human adenovirus 5 DNA," *Virology*, 52:456–467, 1973

Graham and Prevec, "Adenovirus-based expression vectors and recombinant vaccines," *Biotechnology*, 20:363–390, 1992

Graham and Prevec, "Manipulation of adenovirus vector," In: E. J. Murray (ed.), Methods in Molecular Biology: Gene Transfer and Expression Protocol, Clifton, NJ: Humana Press, 7:109–128, 1991

Graham et al., "Characteristics of a human cell line transformed by DNA from human adenovirus type 5", *J. Gen. Virol.*, 36:59–72, 1977

Grunhaus & Horwitz, "Adenovirus as cloning vector," *Seminar in Virology*, 3:237–252, 1992

Hacia et al., "Detection of heterozygous mutations in BRCA1 using high density oligonucleotide arrays and two-colour fluorescence analysis", *Nature Genetics*, 14:441–447, 1996

Hale R. J., et al., "Prognostic Value Of Epidermal Growth Factor Receptor Expression In Cervical Carcinoma," *J. Clin. Pathol.* Voi. 46, pp 149–153 (1993).

Hamada S., et al., "High Expression Rate Of Tn Antigen In Metastatic Lesions Of Uterine Cervical Cancers," *Cancer Lett.*, Vol. 74, pp 167–173 (1993).

Harland and Weintraub, "Translation of mammalian mRNA injected into Xenopus oocytes is specifically inhibited by antisense RNA," *J. Cell Biol.*, 101:1094–1099, 1985

Harlow and Lane, ANTIBODIES: A LABORATORY MANUAL, Cold Spring Harbor Laboratory, Cold Spring Harbor, N.Y., 1988

Harlow, E., Lane, D., 1988. *Antibodies: A LaboratOry Manual*. Cold Spring Harbor Laboratory, Cold Spring Harbor, N.Y.

Harlozinska, A. et al., "Cervical Carcinoma Antigen, Carcinoembryonic Antigen (CEA), And Nonspecific Cross-Reacting Antigen (NCA) In Appraisal Of Uterine Cervix Smears," Am. *J. Clin. Pathol.*, Vol. 83, pp 301–307 (1985).

Hawley R G ; et al., "Association between ICAM-1 expression and metastatic capacity of murine B-cell hybridomas." *Clin Exp Metastasis*, 11 (2) p213–26, 1993.

Heard I., et al, "Papanicolaou Smears In Human Immunodeficiency Virus-Seropositive Women During Follow-Up," *Obstet. Gynecol.*, Vol. 86, pp 749–756 (1995).

Hermonat and Muzycska, "Use of adenoassociated virus as a mammalian DNA cloning vector: Transduction of neomycin resistance into mammalian tissue culture cells," *Proc. Nat. Acad. Sci. U.S.A.*, 81:6466–6470, 1984

Hersdorffer et al., "Efficient gene transfer in live mice using a unique retroviral packaging line," *DNA Cell Biol.*, 9:713–723, 1990

Herz and Gerard, "Adenovirus-mediated transfer of low density lipoprotein receptor gene acutely accelerates cholesterol clearance in normal mice," *Proc. Natl. Acad. Sci. USA* 90:2812–2816, 1993

Hirao T., et al., Antigen, A Marker Of Potential For Metastasis Of Uterine Cervix Cancer Cells," *Cancer*, Vol. 72, pp 154–159 (1993).

Hockenbery, D., "Defining apoptosis", *Am. J. Pathol.*, 146: (1)1–2, 1995

Horwich et al, "Synthesis of hepadenovirus particles that contain replication-defective duck hepatitis B virus genomes in cultured HuH7 cells," *J. Virol.*, 64:642–650, 1990

Innis et al., *PCR Protocols*, Academic Press, Inc., San Diego Calif., 1990

Jayaraman L et al., "Identification of redox/repair protein Ref-1 as a potent activator of p53." *Genes Dev.*, 11 (5) p558–70, 1997

Johnson et al., Peptide Turn Mimetics" IN: *Biotechnology And Pharmacy*, Pezzuto et al., eds., Chapman and Hall, New York, 1993

Jones & Shenk, "Isolation of deletion and substitution mutants of adenovirus type 5," *Cell*, 13:181–188, 1978

Joyce, "RNA evolution and the origins of life," *Nature*, 338:217–244, 1989

Kaneda et al., "Increased expression of DNA cointroduced with nuclear protein in adult rat liver", *Science*, 243:375–378, 1989

Karlsson et al, *EMBO J*, 5:2377–2385, 1986

Kato et al., "Expression of hepatitis B virus surface antigen in adult rat liver", *J. Biol. Chem.*, 266:3361–3364, 1991

Kato H., et al., "Tumor-Antigen TA-4 In The Detection Of Recurrence In Cervical Squamous Cell Carcinoma," *Cancer*, Vol. 54, pp 1544–1546 (1984).

Kato H., et al, "Value Of Tumor-Antigen (TA-4) Of Squamous Cell Carcinoma In Predicting The Extent Of Cervical Cancer," *Cancer*, Vol. 50, pp 1294–1296 (1982).

Kim & Cech, "Three dimensional model of the active site of the self-splicing rRNA precursor or Tetrahymena," *Proc. Natl. Acad. Sci. U.S.A.*, 84:8788–8792, 1987.

Kingma nd Osteroff, "Apurinic sites are position specific topoisomerase II poisons" *J. Biol Chem.*, 272 (2), 1148–1155, 1997.

Klein et al., "High-velocity microprojectiles for delivering nucleic acids into living cells", *Nature*, 327:70–73, 1987

Kohler and Milstein, *Eur. J Immunol.*, 6:511–519, 1976

Kohler and Milstein, *Nature*, 256:495–497, 1975

Kohler M., et al., "The Expression Of EGF Receptor, EGF-Like Factors And C-Myc In Ovarian And Cervical Carcinomas And Their Potential Clinical Significance," *Anticancer Res.*, Vol. 9, pp 1537–1547 (1989).

Koss L. D., "The Papanicolaou Test For Cervical Cancer Detection," *J. Amer. Med. Assoc.*, Vol. 261, pp 737–743 (1989).

Koss L. G., "Cervical (Pap) Smear; New Directions," *Cancer*, Vol. 71, pp 1406–1412 (1993).

Kwoh et al., *Proc. Nat. Acad. Sci. U.S.A.*, 86: 1173, 1989

Kyte & Doolittle, "A simple method for displaying the hydropathic character of a protein," *J. Mol. Biol.*, 157(1):105–132, 1982

Lara, C. et al., "Immunohistochemical Localization Of Filaggrin In Benign, Premalignant And Malignant Cervical Tissue," *Arch. Gynecol. Obstet.*, Vol. 255, pp 73.–79 (1994).

Le Gal La Salle et al., "An adenovirus vector for gene transfer into neurons and glia in the brain," *Science*, 259:988–990, 1993

Levrero et al., *Gene*, 101:195–202, 1991

Lindgren J., et al., "Prognostic Significance Of Tissue Carcinoembryonic Antigen In Mild Dysplasia Of The Uterine Cervix," *Tumcr Biol.*, Vol. 6, pp 465–470 (1986).

Loeb, L. A., "Apurinic Sites As Mutagenic Intermediates", *Cell*, 40:483–484, 1985

Macejak and Sarnow, *Nature*, 353:90–94, 1991

Maniatis, et al., MOLECULAR CLONING: A LABORATORY MANUAL, Cold Spring Harbor Laboratory Press, N.Y., 1989

Mann et al., "Construction of a retrovirus packaging mutant and its use to produce helper-free defective retrovirus", *Cell*, 33:153–159, 1983

Markowitz et al., "A safe packaging line for gene transfer: Separating viral genes on two different plasmids," *J. Virol.*, 62:1120–1124, 1988

Markowitz et al., "A safe packaging line for gene transfer: Separating viral genes on two different plasmids," *J. Virol.*, 62:1120–1124, 1988a Markowitz et al., "Construction and use of a safe and efficient amphotropic packaging cell line," *Virology*, 167:400–406, 1988b McDicken and Rainey, "The Inununohistological Demonstration Of Carcinoembryonic Antigen In Intra-Epithelial And Invasive Squamous Carcinoma Of The Cervix," *Histopathology*, Vol. 7, pp 475–485 (1983).

Merrifield, *Science*, 232: 341–347, 1986

Michel & Westhof, "Modeling of the three-dimensional architecture of group I catalytic introns based on comparative sequence analysis", *J. MoL Biol.*, 216:585–610, 1990

Miller, B. A. et al., (eds.), *SEER Cancer Statistics Review*: 1973–1990. National Cancer institute, NIH Pub. No. 93–2789 (1993).

Mitchell, et al., "Chemoprevention Trials And Surrogate End Point Biomarkers In The Cervix," *Cancer*, Vol. 76, pp 1956–1977 (1995).

Morell N. D., et al, "False-Negative Cytology Rates In Patients In Whom Invasive Cervical Cancer Subsequently Developed," *Obstet. Gynecol*, Vol. 60, pp 41–45 (1982).

Mulligan, "The basic science of gene therapy," *Science*, 260:926–932, 1993

Nicolas & Rubenstein, "Retroviral vectors," In: *Vectors: A survey of molecular cloning vectors and their uses*, Rodriguez & Denhardt (eds.), Stoneham: Butterworth, 493–513, 1988

Nicolau and Sene, "Liposome-mediated DNA transfer in eukaryotic cells," *Biochim. Biophys. Acta*, 721:185–190, 1982

Nicolau et al., "Liposomes as carriers for in vivo gene transfer and expression," *Methods Enzymol.*, 149:157–176, 1987

Ohara et al., *Proc. Nat'l Acad. Sci. U.S.A.*, 86: 5673–5677, 1989

Okazaki, et al., "A Redox Factor Protein, Ref1, Is Involved In Negative Gene Regulation By Extracellular Calcium", *J. Biol. Chem.*, 269:27855–27862, 1994

Parham and Hicks, "Gynecologic Cancer Among The Socioeconomically Disadvantaged, " *Cancer*, Vol. 76, pp 2176–2180 (1995).

Park T. W., et al., "Molecular Biology Of Cervical Cancer And Its Precursors," *Cancer*, Vol. 76, pp 1902–1913 (1995).

Paskind et al., Dependence of moloney murine leukemia virus production on cell growth. *Virology*, 67:242–248, 1975

Pease et al, Light-generated oligonucleotide arrays for rapid DNA sequence analysis. *Proc. Natl. Acad. Sci. U.S.A.*, 91:5022–5026, 1994

Pelletier and Sonenberg, *Nature*, 334:320–325, 1988

Perales et al., "Gene transfer in vivo: Sustained expression and regulation of genes introduced into the liver by receptor-targeted uptake", *Proc. Natl. Acad. Sci.* 91:4086–4090, 1994

Pignon et al., *Hum. Mutat.*, 3: 126–132, 1994

Potter et al., "Enhancer-dependent expression of human k immunoglobulin genes introduced into mouse pre-B lymphocytes by electroporation," *Proc. Nat. Acad. Sci. U.S.A.*, 81:7161–7165, 1984

Racher et al., *Biotechnology Techniques*, 9:169–174, 1995

Ragot et al., "Efficient adenovirus-mediated transfer of a human minidystrophin gene to skeletal muscle of mdx mice," *Nature*, 361:647–650, 1993

Raju G.C., "Expression Of The Cytokeratin Marker CAM 5.2 In Cervical Neoplasia," *Histopathology*, Vol. 12, pp 437–443 (1988).

Raju G.C., "Expression Of The Proliferating Cell Nuclear Antigen In Cervical Neoplasia," *Int. J GynecoL PathoL*, Vol. 13, pp 337–341 (1994).

Reinhold-Hurek & Shub, "Self-splicing introns in tRNA genes of widely divergent bacteria," *Nature*, 357:173–176, 1992

Renan, "Cancer genes: Current status, future prospects and applications in radiotherapy/oncology," *Radiother. Oncol.*, 19:197–218, 1990

Rich et al., "Development and analysis of recombinant adenoviruses for gene therapy of cystic fibrosis," *Hum. Gene Ther.*, 4:461–476, 1993

Richard R. M., "Screening; The Next Century," *Cancer*, Vol. 76, pp 1919–1927 (1995).

Ridgeway, "Mammalian expression vectors," In: Rodriguez R L, Denhardt D T, ed. Vectors: A survey of molecular cloning vectors and their uses. Stoneham: Butterworth, 467–492, 1988

Rippe et al., "DNA-mediated gene transfer into adult rat hepatocytes in primary culture," Mol. Cell Biol., 10:689–695, 1990

Rosenfeld et al., "Adenovirus-mediated transfer of a recombinant α1-antitrypsin gene to the lung epithelium in vivo," Science, 252:431–434, 1991

Rosenfeld et al., "In vivo transfer of the human cystic fibrosis transmembrane conductance regulator gene to the airway epithelium," Cell, 68:143–155, 1992

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses", Proc. Nat'l Acad. Sci. U.S.A., 86:9079–9083, 1989.

Rutenan, E. M. et al., "Carcinoembryonic Antigen In Malignant And Nonmalignant Tumors," Cancer, Vol. 42, pp 581–590 (1978).

Sainz, C. R. et al, "LA-1 Oncogene. A Possible New Prognostic Index For Evaluating Cervical Squamous Intraepithelial Lesions," J. Reprod. Med., Vol. 38, pp 173–178 (1993).

Sambrook et al., Molecular Cloning: A Laboratory Manual, 2d Ed., Cold Spring Harbor Laboratory Press, Cold Spring Harbor, NY, 1989

Sarker, A. B. et al., "Tumor Marker Studies Of Cervical Smears: An Immunohistochemical Approach," Indian J. Pathol Micropol., Vol. 37, pp 45–51 (1994).

Sarver et al., "Ribozymes as potential anti-HIV-1 therapeutic agents," Science, 247:1222–1225, 1990

Scanlon et al., "Ribozyme-mediated cleavages of c-fos mRNA reduce gene expression of DNA synthesis enzymes and metallothionein," Proc Natl Acad Sci USA., 88:10591–10595, 1991

Schiffman M. H., L. A. Brinton, "The Epidemiology Of Cervical Carcinogenesis," Cancer, Vol. 76, pp 1888–1901 (1995).

Shoemaker et al, "Quantitative phenotypic analysis of yeast deletion mutants using a highly parallel molecular barcoding strategy", Nature Genetics 14:450–456, 1996

Sideri M., et al., "Operator Variability In Disease Detection And Grading By Colposcopy In Patients With Mild Dysplastic Smears," Cancer, Vol. 76, pp 1601–1605 (1995).

Steinbeck R. G., et al., "The Relationship Between Proliferating Cell Nuclear Antigen (PCNA), Nuclear DNA Content And Mutant p53 During Genesis Of Cervical Carcinoma," Acts Oncol, Vol. 34, pp 171–176 (1995).

Stewart and Young, Solid Phase Peptide Synthesis, 2d. ed., Pierce Chemical Co., 1984

Stratford-Perricaudet & Perricaudet, "Gene transfer into animals: the promise of adenovirus," In: HUMAN GENE TRANSFER, Cohen-Haguenauer & Boiron (eds.), Editions John Libbey Eurotext, France, 51–61, 1991

Suehiro Y., et al, "Flow Cytometric Analysis Of Tumor Antigen TA-4 In Cervical Cytologic Specimens," Cancer, Vol. 56, pp 1380–1384 (1986).

Tam et al., J. Am. Chem. Soc., 105:6442, 1983

Temin, "Retrovirus vectors for gene transfer: Efficient integration into and expression of exogenous DNA in vertebrate cell genome," In: GENE TRANSFER, Kucherlapati (ed.), New York: Plenum Press, 149–188, 1986

Tervahauta, A. et al., "Epidermal Growth Factor Receptor, C-ErbB-2 Proto-Oncogene And Estrogen Receptor Expression In Human Papillomavirus Lesions Of The Uterine Cervix," Int. J. Gynecol. Pathol., Vol. 13, pp 234–240 (1994).

Tervahauta, A.I. et al., "Expression Of p53 Protein Related To The Presence Of Human Papillomavirus (HPV) DNA In Genital Carcinomas And Precancer Lesions," Anticancer Res., Vol. 13, pp 1107–1111 (1993).

Terzano P., et al., "Immunohistochemistry With Antibody To The LA-1 Oncogene As A Prognostic Marker In Cervical Intraepithelial Neoplasia," Gynecol. Oncol., Vol. 48, pp 317–327 (1993).

Toki T., A. Yajima, "Immunohistochemical Localization Of Carcinoembryonic Antigen (CEA) In Squamous Cell Carcinoma Of The Uterine Cervix: Prognostic Significance Of Localization Pattern Of CEA," Tohoku J. Exp. Med., Vol. 165, pp 25–32 (1991).

Top et al, "Immunization with live types 7 and 4 adenovirus vaccines. II. Antibody response and protective effect against acute respiratory disease due to adenovirus type 7," J. Infect. Dis., 124:155–160, 1971

Tur-Kaspa et al., "Use of electroporation to introduce biologically active foreign genes into primary rat hepatocytes", Mol. Cell Biol., 6:716–718, 1986 van Nagell J. R., et al., "Carcinoembryonic Antigen In Carcinoma Of The Uterine Cervix: Antigen Distribution In Primary And Metastatic Tumors," Cancer, Vol. 49, pp 379–383 (1982).

Varmus et al., "Retroviruses as mutagens: Insertion and excision of a nontransforming provirus alter the expression of a resident transforming provirus," Cell, 25:23–36, 1981

Wagner et al., Science, 260:1510–1513, 1990

Walker et al., Proc. Nat'l Acad. Sci. U.S.A 89:392–396 1992

Wilson, et al., "Differential expression of the apurinic/apyrimidinic endonuclease (APE/ Ref-1) multifunctional DNA base excision repair gene during fetal development and in adult rat brain and testis., Mutat. Res. 362:237–248, 1996

Wilson, et al., "Drosophila ribosomal protein S3 contains an activity that cleaves DNA at apurinic/apyrimidinic sites, J. of Biol. Chem. 269:25359–64, 1994

Wilson, et al., "Differential Cellular Expression Of The Human MSH2 Repair Enzyme In Small And Large Intestine", Cancer Res., 55:5146–5150, 1995

Wilson, et al., "Drosophila Ribosomal Protein S3 Contains An Activity That Cleaves DNA At Apurinic/apyrimidinic Sites", J. Biol Chem., 269:25359–25367, 1994

Wong et al, "Appearance of β-lactamase activity in animal cells upon liposome mediated gene transfer," Gene, 10:87–94, 1980

Wright T. C., Jr., et al, and the New York Cervical Disease Study, "Cervical Intraepithelial Neoplasia In Women Infected With Human Immunodeficiency Virus: Prevalence, Risk Factors, And Validity Of Papanicolaou Smears," Obstet. Gynecol., Vol. 84, pp 591–597 (1994).

Wu and Wu, "Evidence for targeted gene delivery to HepG2 hepatoma cells in vitro," Biochemistry, 27:887–892, 1988

Wu and Wu, "Receptor-mediated in vitro gene transfections by a soluble DNA carrier system," J. Biol. Chem., 262:4429–4432, 1987

Wu and Wu, Adv. Drug Delivery Rev., 12:159–167, 1993

Wu et al., Genomics, 4:560, 1989

Xanthoudakis, et al, "Redox Activation Of Fos-Jun DNA Binding Activity Is Mediated By A DNA Repair Enzyme", EMBO J., 11:3323–3335, 1992

Yang et al., "In vivo and in vitro gene transfer to mammalian somatic cells by particle bombardment," *Proc. Natl. Acad. Sci U.S.A.*, 87:9568–9572, 1990

Zelenin et al, High-velocity mechanical DNA transfer of the chloramphenicol acetyltransferase gene into rodent liver, kidney and mammary gland cells in organ explants and in vivo. *FEBS Lett.*, 280:94–96, 1991.

What is claimed is:

1. A method for identifying a premalignant or malignant condition in a human subject comprising determining the level of apurinic/apyrimidinic endonuclease (APE) in cells from a sample from said human subject, wherein an elevated level of APE, as compared to the APE level in corresponding normal cells, indicates a premalignant or malignant condition in said human subject.

2. The method of claim 1, wherein said sample is selected from the group consisting of skin, muscle, facia, brain, prostate, breast, endometrium, lung, pancreas, small intestine, blood cells, liver, testes, ovaries, cervix, colon, skin, stomach, esophagus, spleen, lymph node, bone marrow, kidney, peripheral blood, lymph fluid, ascites, serous fluid, pleural effusion, sputum, cerebrospinal fluid, lacrimal fluid, stool and urine.

3. The method of claim 1, wherein said premalignancy or malignancy is in a tissue selected from the group consisting of brain, lung, liver, spleen, kidney, lymph node, small intestine, pancreas, blood cells, colon, stomach, breast, endometrium, cervix, prostate, testicle, ovary, skin, head and neck, esophagus, bone marrow and blood tumor cells.

4. The method of claim 1, wherein said deteimnig comprises evaluating APE protein levels.

5. The method of claim 1, wherein said determining comprises evaluating APE transcript levels.

6. The method of claim 4, wherein said evaluating comprises an immunoassay.

7. The method of claim 5, wherein said evaluating comprises quantitative reverse transcription-polymerase chain reaction (RT-PCR).

8. A method for determining the premalignant or malignant state of a cell comprising determining the level of APE in said cell, wherein an elevated level of APE, as compared to the APE level in a corresponding normal cell, indicates a premalignant or malignant state in said cell.

9. The method of claim 8, wherein said determining comprises the steps of:
   (i) disrupting said cell;
   (ii) contacting said disrupted cell with an antibody that reacts immunologically with APE; and
   (iii) quantitating the amount of APE bound to said antibody.

10. The method of claim 9, wherein said cell is disrupted by detergent lysis, freeze-thaw, sonication, osmotic shock or manual rupture.

11. The method of claim 9, wherein said quantitating is by linked immunosorbant assay (ELISA).

12. The method of claim 9, wherein said quantitating is by radioimmunoassay (RIA).

13. The method of claim 8, wherein said determining comprises the steps of:
   (i) isolating mRNA from said cell;
   (ii) subjecting said mRNA to reverse transcription to produce cDNA; and
   (iii) quantitating APE cDNA by polymerase chain reaction (PCR).

14. A method for diagnosis of premalignant or malignant condition in a human subject which comprises:
   (i) administering to the subject an imaging agent comprising antibodies which react immunologically with APE bound to a label which is detectable by an external scan of the subject; and
   (ii) externally scanning the subject to determine whether there is a localized concentration of the imaging agent.

15. The method of claim 14 wherein the label is a radioactive label or is detectable by an X-ray, positron emission or magnetic resonance image scanning of the subject.

* * * * *

UNITED STATES PATENT AND TRADEMARK OFFICE
CERTIFICATE OF CORRECTION

PATENT NO.   :   5,919,643

DATED         :   July 6, 1999

INVENTOR(S)  :   Mark R. Kelley, John Duguid; John Eble

It is certified that error appears in the above-identified patent and that said Letters Patent is hereby corrected as shown below:

In claim 11, column 81, line 23, insert --enzyme-- after "by".

Signed and Sealed this

Twenty-fifth Day of January, 2000

Attest:

*Attesting Officer*         *Acting Commissioner of Patents and Trademarks*